US008635746B2

(12) United States Patent
Bellamy et al.

(10) Patent No.: US 8,635,746 B2
(45) Date of Patent: Jan. 28, 2014

(54) CLOSURE LATCH

(75) Inventors: Alexander Harrison Bellamy, Bothell, WA (US); Richard Radford, Auburn, WA (US); Mark Charbonneau, Bellevue, WA (US); Drew Radford, Seattle, WA (US); Judith Marquardt, Arlington, WA (US)

(73) Assignee: Cenorin, LLC, Kent, WA (US)

( * ) Notice: Subject to any disclaimer, the term of this patent is extended or adjusted under 35 U.S.C. 154(b) by 243 days.

(21) Appl. No.: 13/081,404

(22) Filed: Apr. 6, 2011

(65) Prior Publication Data
US 2011/0247179 A1 Oct. 13, 2011

Related U.S. Application Data

(60) Provisional application No. 61/322,708, filed on Apr. 9, 2010.

(51) Int. Cl.
*A44B 11/12* (2006.01)
(52) U.S. Cl.
USPC ............................ 24/170; 24/193; 24/265 BC
(58) Field of Classification Search
USPC ...... 24/168, 170, 191, 193, 265 BC, 265 EC; 606/203
See application file for complete search history.

(56) References Cited

U.S. PATENT DOCUMENTS

| | | | |
|---|---|---|---|
| 438,912 A | 10/1890 | Day | |
| 1,245,749 A * | 11/1917 | McGee | 24/191 |
| 1,962,285 A | 6/1934 | Robinson | |
| 2,287,722 A * | 6/1942 | Beazley | 24/170 |
| 2,573,791 A | 11/1951 | Howells | |
| 2,622,293 A * | 12/1952 | Wermlinger | 24/170 |
| 2,882,903 A | 4/1959 | Ramien | |
| 2,981,993 A * | 5/1961 | Elsner | 24/170 |
| 2,998,626 A * | 9/1961 | Prete, Jr. | 24/170 |
| 3,328,856 A * | 7/1967 | Jonas | 24/191 |
| 3,344,486 A * | 10/1967 | Eveland | 24/194 |
| 3,741,203 A | 6/1973 | Liman | |
| 4,224,935 A | 9/1980 | Metelnick | |
| 4,433,486 A | 2/1984 | Muehlenbein | |
| 4,640,281 A | 2/1987 | Strum et al. | |
| 4,727,864 A | 3/1988 | Wiesenthal et al. | |
| 4,911,151 A | 3/1990 | Rankin et al. | |
| 4,932,104 A | 6/1990 | Kowal | |
| 5,083,557 A | 1/1992 | Lennon et al. | |
| 5,152,282 A | 10/1992 | Elphick et al. | |
| 5,314,437 A | 5/1994 | Holtsch | |
| 5,372,565 A | 12/1994 | Burdenko | |
| 5,439,438 A | 8/1995 | Ersfeld et al. | |
| 5,621,953 A * | 4/1997 | Fildan | 24/170 |
| 5,840,675 A | 11/1998 | Yeazell | |
| 6,640,460 B1 | 11/2003 | Nabarro et al. | |

(Continued)

OTHER PUBLICATIONS

File History for U.S. Appl. No. 11/525,593, Application published Mar. 27, 2008.

*Primary Examiner* — Robert J Sandy
*Assistant Examiner* — Abigail E Morrell
(74) *Attorney, Agent, or Firm* — Knobbe Martens Olson & Bear LLP

(57) ABSTRACT

The present disclosure relates generally to closure mechanisms, such as a closure latch device for clamping a band. The closure latch comprises a first and second latch member engaged to pivot relative to each other. Certain embodiments relate to methods of clamping a band. Certain embodiments relate to methods of manufacturing a clamping device.

19 Claims, 25 Drawing Sheets

(56) References Cited

U.S. PATENT DOCUMENTS

| | | |
|---|---|---|
| 6,664,434 B2 | 12/2003 | Cominsky |
| 6,735,826 B2 * | 5/2004 | Uehara et al. .................. 24/170 |
| 6,787,680 B2 | 9/2004 | McGowan et al. |
| 6,875,199 B2 | 4/2005 | Altman |
| 7,265,256 B2 | 9/2007 | Artenstein |
| 7,370,392 B2 | 5/2008 | Holtsch |
| 7,478,459 B2 * | 1/2009 | Kawaguchi et al. ............ 24/170 |
| 2001/0018566 A1 | 8/2001 | Masini |
| 2003/0036715 A1 | 2/2003 | Knutson et al. |
| 2003/0109819 A1 | 6/2003 | Tsuruda et al. |
| 2003/0172499 A1 * | 9/2003 | Uehara et al. .................. 24/170 |
| 2003/0191424 A1 | 10/2003 | Skinner |
| 2004/0133136 A1 | 7/2004 | Lassalle et al. |
| 2004/0199092 A1 | 10/2004 | Biewend et al. |
| 2004/0215117 A1 | 10/2004 | Gorman |
| 2005/0027227 A1 | 2/2005 | Dumas et al. |
| 2005/0107732 A1 | 5/2005 | Boyde |
| 2005/0211590 A1 | 9/2005 | McClure et al. |
| 2005/0256466 A1 | 11/2005 | Winkler |
| 2006/0116621 A1 | 6/2006 | Barker |
| 2006/0129080 A1 | 6/2006 | Bjornberg et al. |
| 2006/0258969 A1 | 11/2006 | Brown et al. |
| 2007/0193004 A1 | 8/2007 | Chou |
| 2007/0226961 A1 * | 10/2007 | Anderson et al. ............... 24/170 |
| 2007/0240286 A1 * | 10/2007 | Kawaguchi et al. ............ 24/191 |
| 2008/0077064 A1 | 3/2008 | Bockol et al. |
| 2009/0287122 A1 | 11/2009 | Evans |

* cited by examiner

CLOSURE LATCH

CROSS REFERENCE TO RELATED APPLICATIONS

This application claims priority to U.S. Provisional Patent Application No. 61/322,708, filed Apr. 9, 2010, entitled CLOSURE LATCH, which is hereby incorporated herein by reference in its entirety.

BACKGROUND OF THE INVENTION

1. Field of the Invention

The present disclosure relates generally to closure mechanisms, such as a latch for clamping a band. Certain embodiments relate to closure latch devices. Certain embodiments relate to closure latch devices including a band. Certain embodiments relate to methods of clamping a band. Certain embodiments relate to methods of manufacturing a clamping device.

2. Description of the Related Art

Many types of closure mechanisms exist in the art. However, it is difficult to design a closure latch that is convenient to use and manufacture, while providing sufficient clamping force when used with a band.

SUMMARY

One embodiment provides a closure latch comprising a first latch member. The first latch member comprises a band attachment portion configured to secure a portion of a band to the first latch member, a first clamping surface. The closure latch further comprises a second latch member engaged with the first latch member such that the first and second latch members can pivot relative to each other about a pivot axis. The second latch member comprises a second clamping surface. A first portion of a band can be secured to the band attachment portion of the first latch member while a second portion of the band is positioned between the first and second clamping surfaces, such that tension in the band between the first and second band portions causes the first band portion to pull the first latch member, which in turn causes the first latch member to rotate about the pivot axis towards the second latch member, which in turn causes the first and second clamping surfaces to clamp onto the second band portion.

Another embodiment provides a closure latch comprising a first latch member, a second latch member and a latch resistance element. The first latch member comprises a first clamping surface. The second latch member is engaged with the first latch member such that the first and second latch members can pivot relative to each other about a pivot axis. The second latch member comprises a second clamping surface. The first latch member can rotate in a first direction with respect to the second latch member about the pivot axis to a closed position in which the first and second clamping surfaces clamp together. The first latch member can rotate about the pivot axis in a second direction with respect to the second latch member to an open position wherein the first and second clamping surfaces do not clamp together. The latch resistance element is configured to hold the first latch member in the open position with respect to the second latch member. The latch resistance element is configured to release the first latch member from the open position when a force tending to move the first latch member to the closed position is greater than or equal to a breakaway force associated with the latch resistance element.

Another embodiment provides a method of clamping a band, comprising pivoting a first latch member relative to a second latch member about a pivot axis, the first latch member engaged with the second latch member, the first latch member comprises a first clamping surface, the second latch member comprises a second clamping surface, a first portion of a band secured to the first latch member. The method further comprises positioning a second portion of the band between the first and second clamping surfaces. The method further comprises providing tension to the band between the first and second band portions, which in turn causes the first latch member to rotate about the pivot axis towards the second latch member, which in turn causes the first clamping surface and the second clamping surface to clamp onto the second band portion.

Another embodiment provides a clamping device comprising an elastic band with a first band tension marker and a second band tension marker spaced apart along a portion of a length of the band. The first band tension marker and the second band tension marker are separated by a tension marker distance that varies as the elastic band is stretched or relaxed. The clamping device further comprises a first latch member, a second latch member engaged with the first latch member and movable between clamped and unclamped positions relative to the first latch member. A portion of the elastic band can be clamped between the first and second latch members when the second latch member is in the clamped position. The clamping device further comprises a first band tension indicator and a second band tension indicator spaced apart by a tension indicator distance along a portion of the first latch member or the second latch member. A user of the clamping device can stretch the elastic band to a predetermined target tension by adjusting the tension marker distance to be approximately equal to the tension indicator distance.

Another embodiment provides a method of manufacturing a clamping device comprising marking an elastic band with a first band tension marker and a second band tension marker spaced apart along a portion of a length of the band, the first band tension marker and the second band tension marker separated by a tension marker distance that varies as the elastic band is stretched or relaxed. The method further comprises engaging a first latch member with a second latch member, the second latch member movable between clamped and unclamped positions relative to the first latch member, wherein a portion of the elastic band can be clamped between the first and second latch members when the second latch member is in the clamped position. The method further comprises providing a first band tension indicator and a second band tension indicator spaced apart by a tension indicator distance, wherein a user of the clamping device can stretch the elastic band to a predetermined target tension by adjusting the tension marker distance to be approximately equal to the tension indicator distance.

Another embodiment provides a closure latch. The closure latch comprises a first latch member comprising a first clamping surface and a second latch member engaged with the first latch member such that the first and second latch members can pivot relative to each other about a pivot axis, the second latch member comprising a second clamping surface. The first latch member can rotate in a first direction with respect to the second latch member about the pivot axis to a closed position wherein the first and second clamping surfaces clamp a first portion of a band. The first latch member can rotate about the pivot axis in a second direction with respect to the second latch member to an open position wherein the first and second clamping surfaces do not clamp the first portion of the band. A second portion of the band forms a loop which can be tightened around an object by pulling the first portion of the band, wherein the first portion of the band does not substantially contact the first or second latch members when the first latch member is in an unclamped position.

For purposes of summarizing the invention and the advantages achieved over the prior art, certain objects and advantages of the invention have been described above and as further described below. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other aspects of the invention will be readily apparent from the following description and from the appended drawings (not necessarily to scale), which are meant to illustrate and not to limit the invention, and in which.

DETAILED DESCRIPTION OF THE DRAWINGS

The present disclosure relates generally to closure mechanisms, such as a latch for clamping a band. Certain embodiments relate to closure latch devices. Certain embodiments relate to closure latch devices including a band. Certain embodiments relate to methods of clamping a band. Certain embodiments relate to methods of manufacturing a clamping device.

Figure 1:
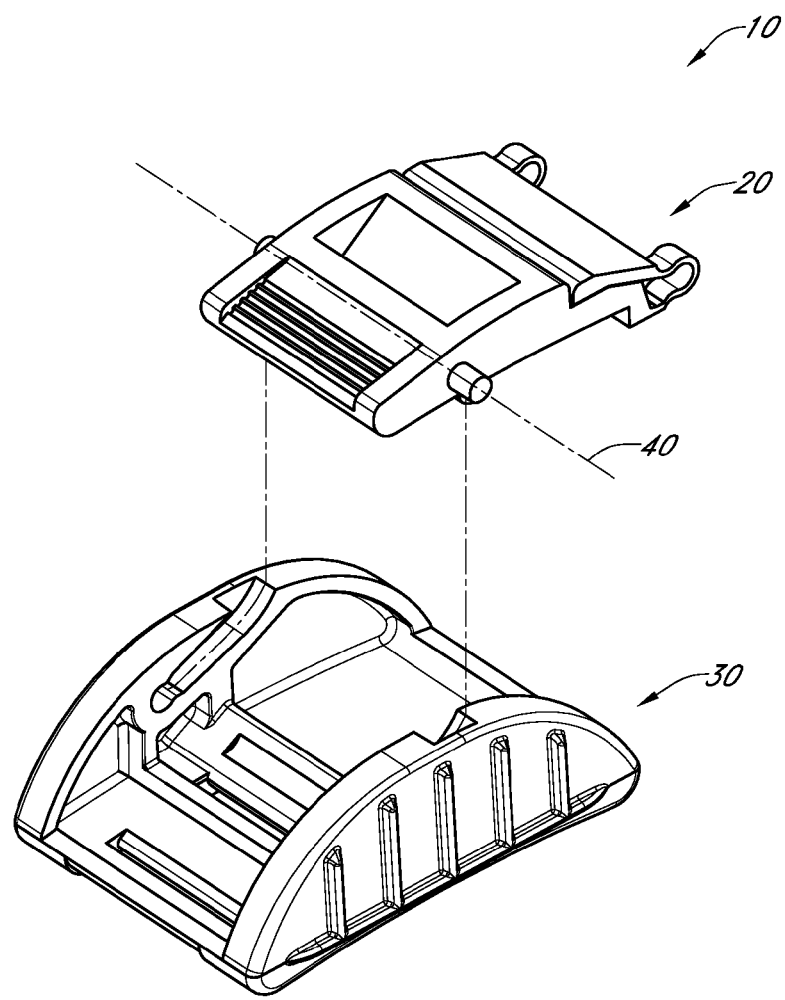
FIG. 1 shows a front and right side perspective and exploded view of an embodiment of a closure latch.

FIG. 1 shows a front and right side perspective and exploded view of an embodiment of a closure mechanism, such as a latch, buckle, clasp, or the like, illustrated here as a closure latch 10. The closure latch 10 can comprise a first latch member 20 engaged with a second latch member 30, such that the first latch member 20 and the second latch member 30 can pivot relative to each other about a pivot axis 40. In some embodiments, the first latch member 20 can be removably engaged with the second latch member 30.

Figure 2:
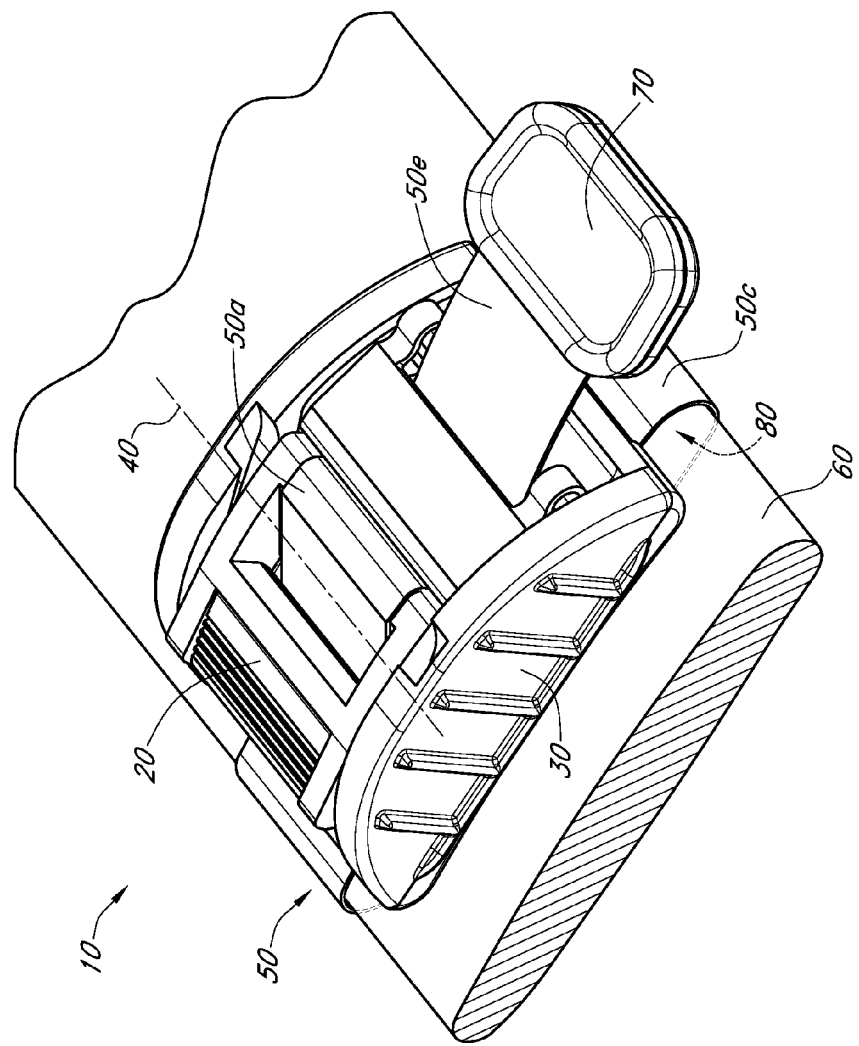
FIG. 2 shows a front and left side perspective view of the closure latch of FIG. 1 in an exemplary environment of use.

FIG. 2 shows a front and left side perspective view of the closure latch 10 of FIG. 1 in an exemplary environment of use. The closure latch 10 can be used to releasably hold a portion of a strap, webbing, band, belt, leash, strip, string, rope, or any other band or strap-like structure, illustrated here as an exemplary band 50, at least partially around one or more objects 60. Preferably, the closure latch 10 can hold a portion of the band 50 in tension around object 60. Even more preferably, the closure latch 10 can hold a portion of the band 50 stretched and in tension around the object 60.

The object 60 can be any object or plurality of objects, animate or inanimate, around which a user wraps or secures a portion of the band 50. In some environments of use, closure latch 10 can be configured to apply and hold the band 50 around the perimeter or circumference of a user or patient's appendage, e.g., to form a tourniquet around a patient's arm or leg. As used herein, the term "circumference" does not necessarily imply circularity, unless so indicated. In another environment of use, one or more closure latches 10 can be configured to hold an intermediary structure, e.g., a medical barrier (not shown), between the band 50 and the patient's appendage, such as medical barrier embodiments described in co-owned U.S. Provisional Patent Application No. 61/320,886, the entirety of which is herein incorporated by reference. It will be understood that "patient" as used herein is not limited to humans or any particular species of animal, and the embodiments of the closure latch 10 described herein can be used on non-human animals.

A first portion of the band 50, illustrated as an attached band portion 50a (e.g., the proximal end of band 50), can be attached to the first latch member 20, with a remaining portion of the band 50 routed through the first latch member 20, through the second latch member 30, and extending at least partially around the object 60. The band 50 can comprise a second portion 50e that can be pulled, to apply tension to, and in some embodiments stretch, band 50, preferably at an end opposing the band attachment portion 50a; e.g., the distal, or free end of the band. An optional clip, clasp or other structure, such as clip 70, can be secured to the free end portion 52 of the band 50, to allow a user to easily grasp and tighten band 50, and to prevent the free end 50*e* from being pulled back through latch 10 while in use.

The latch 10 can be used to hold an object inserted into a loop 80 that can be formed within a third portion 50*c* of the band 50. It will be understood that although some embodiments described herein include a continuous band 50 routed through the latch 10, and with a loop 80 around the object 60, the invention is not limited to such embodiments. For example, the band 50 can be comprise two or more separate pieces, with each piece attached at one end to closure latch 10, and attached at the opposing end to a separate structure, such as object 60, or some other intermediate structure to be secured around object 60 (e.g., a medical barrier).

It will also be understood that although many of the embodiments herein describe the use of closure latch 10 in conjunction with the band 50, the closure latch 10 can be manufactured and provided independently without a band or strap. Thus, the invention is not to be limited to require the band with the closure latch. In some embodiments, the closure latch 10 can be provided to a user without a band 50, and the user can provide a separate band to be used with the latch 10. The closure latch 10 and the band 50 can also be supplied as a kit, wherein the closure latch 10 and the band 50 can be supplied separately and then assembled by the user.

The exemplary band 50 can comprise any of many flexible, and in some embodiments, stretchable or elastic material known in the art, with sufficient strength to hold the object 60 under a desired tension. The band 50 can comprise any of many different types of films, membranes, or substrates. The band 50 may be any of myriad compositions suitable for short-term or long-term contact with a user's skin. The band 50 can comprise a waterproof, water-resistant, or hydrophilic material. In some embodiments, any portion of the band 50 can be coated, for example, with pharmaceutical or other therapeutical treatments to improve the comfort and health of the user. The band 50 may comprise one or more layers of material, and may comprise one or more materials along its length or width. The band 50 may alternatively or additionally be comprised of polymers, plastics, and water-vapor-breathable films, layers, and materials. The band 50 may be any color, clear or opaque to any degree, and may be printed, for example, with brand or source identification, constructions or application, aesthetic decorations, and the like. In some embodiments, the band 50 can be marked with tension markers, as described further herein. In a preferred embodiment, the band 50 can comprise various materials known to the industry that can provide adequate elasticity to compress against the user's appendage 60 when the band 50 is in tension around such appendage, such as natural or synthetic rubber materials. In a further preferred embodiment, the band 50 comprises polyisoprene.

Figure 3:
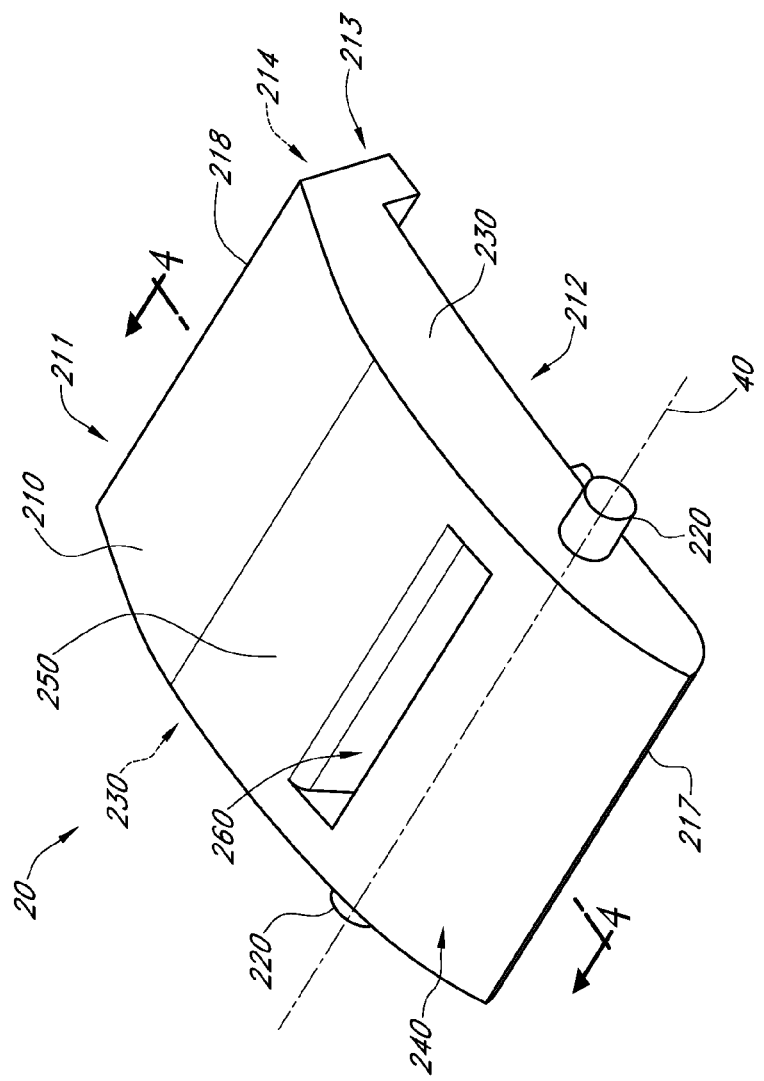
FIG. 3 shows a front and right side perspective view of an embodiment of the first latch member of the closure latch of FIG. 1.
Figure 4:
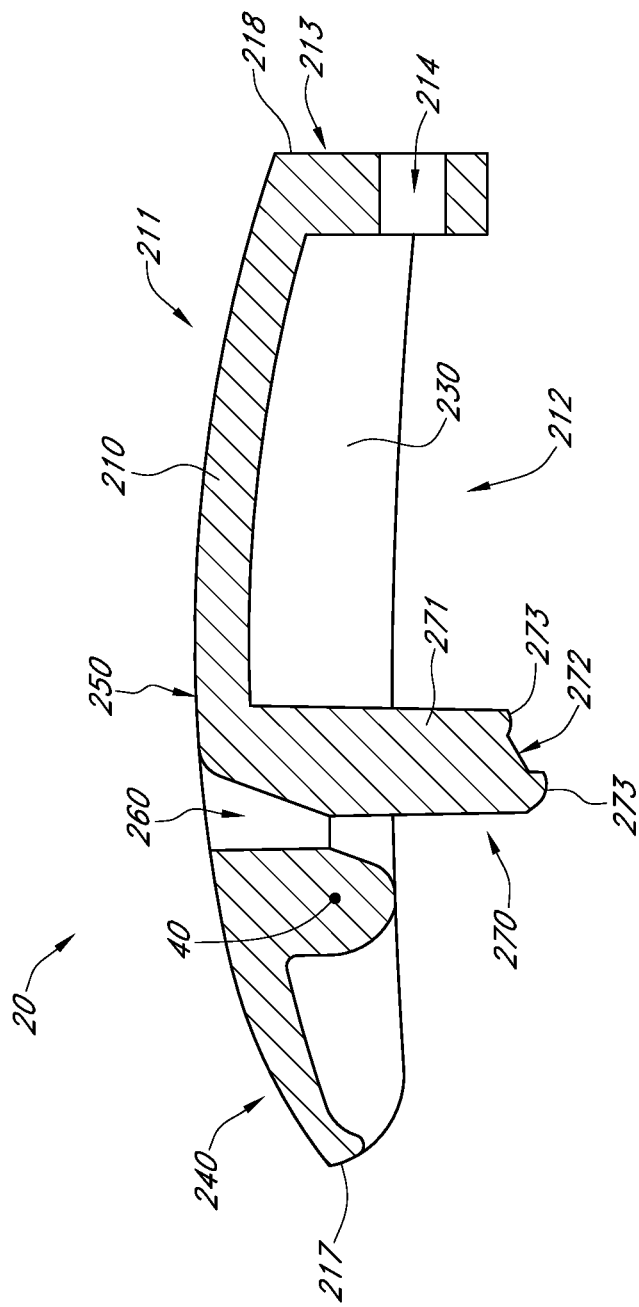
FIG. 4 shows a side cross-sectional view of an embodiment of the first latch member taken along line 4-4 of FIG. 3.

FIG. 3 shows a front and right side perspective view of an embodiment of the first latch member 20 of the closure latch 10 of FIG. 1. FIG. 4 shows a side cross-sectional view of an embodiment of the first latch member 20 taken along line 4-4 of FIG. 3. First latch member 20 can comprise a body 210 configured to pivot first latch member 20 relative to second latch member 30 about the pivot axis 40, as described above and shown in FIGS. 1 and 2. Body 210 can comprise an upper side 211 that generally faces away from second latch member 30, and a lower side 212 that generally faces towards second latch member 30 when first latch member 20 is engaged with second latch member 30. Body 210 can comprise any of many shapes, such as an approximately rectangular, ovular, trapezoidal, or other cross sectional shapes. In a preferred embodiment, body 210 comprises an approximately rectangular-shaped structure. In a further preferred embodiment, body 210 comprises a curved top and/or bottom surface, and more preferably, a convex top and/or concave bottom surface.

First latch member 20 can comprise one or more rotational members 220 to allow first member 20 to pivot about pivot axis 40 relative to second latch member 30 (FIGS. 1 and 2). Rotational member 220 can comprise any of many structures known in the art to permit rotational movement, such as a hub, bearing, hinge, pin, ball and pinion, axle, rotational joint, clutch, disc, gears, and the like. In a preferred embodiment, rotational members 220 can comprise a pair of substantially cylindrical members, each extending from an opposing sidewall 230 of body 210, with a centerline substantially aligned with pivot axis 40. Rotational members 220 can extend outwardly from sidewalls 230, although in some embodiments, members 220 can extend inwardly from sidewalls 230. Rotational members 220 (and thus, pivot axis 40) can be positioned anywhere along the length of body 210. In a preferred embodiment, rotational members 220 and pivot axis can be positioned proximate to a proximal end 217 of body 210, such that body 210 pivots approximately about its front proximal end 217.

Closure latch 10 can include various handling portions integrated into or attached to first latch member 20 and/or second latch member 30 to allow a user to easily grasp and move first latch member 20 and/or second latch member 30. These handling portions can include various tabs, knobs, dimples, nipples, surface textures and contours (e.g., concave protrusions and convex recessions), ribs, slots, grooves, and the like, spanning across various portions of members 20 and/or 30. These handling portions can comprise one or more materials that may improve a user's grip on closure latch 10, such as various textured frictional coatings, or resilient materials, such as rubber or foam. In some embodiments, the body 210 of first latch member 20 can comprise an optional handling portion 240 proximate to an end (e.g., proximal end 217) of the body 210, and preferably extending proximally relative to rotational members 220. Handling portion 240 can comprise many different shapes and configurations, such as a smooth, unbroken surface relative to a top surface of body 210. In a preferred embodiment, handling portion 240 can comprise a surface 241 tapered downwardly relative to sidewalls 230 and the remainder of body 210 (see, e.g., FIGS. 5-6). In another preferred embodiment, surface 241 comprises a texture or surface contour, such as ribs 241.

Figure 10A:
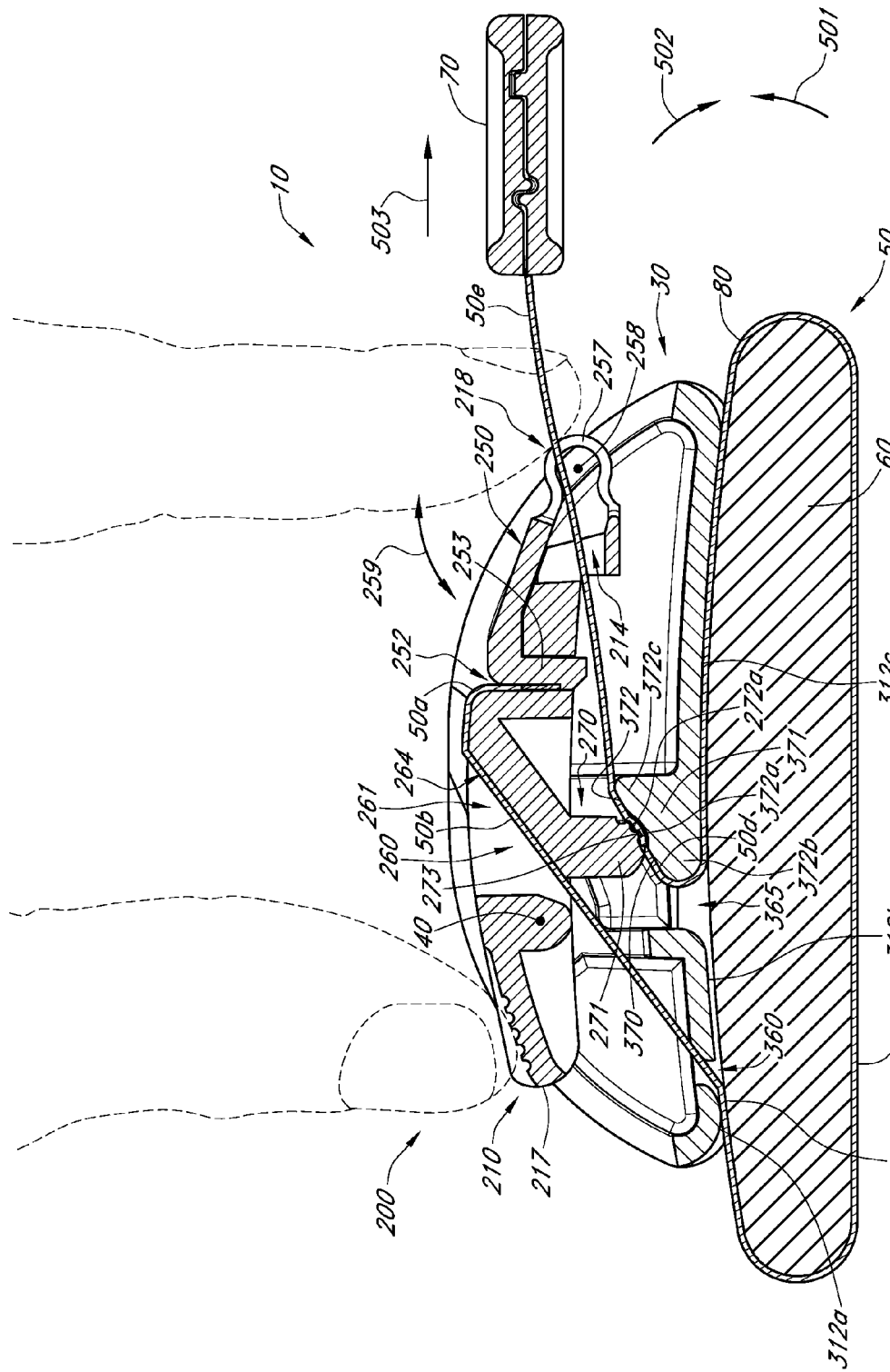
FIGS. 10A and 10B illustrate a method of using an embodiment of a closure latch to clamp and unclamp, respectively, a portion of a band.
Figure 10B:
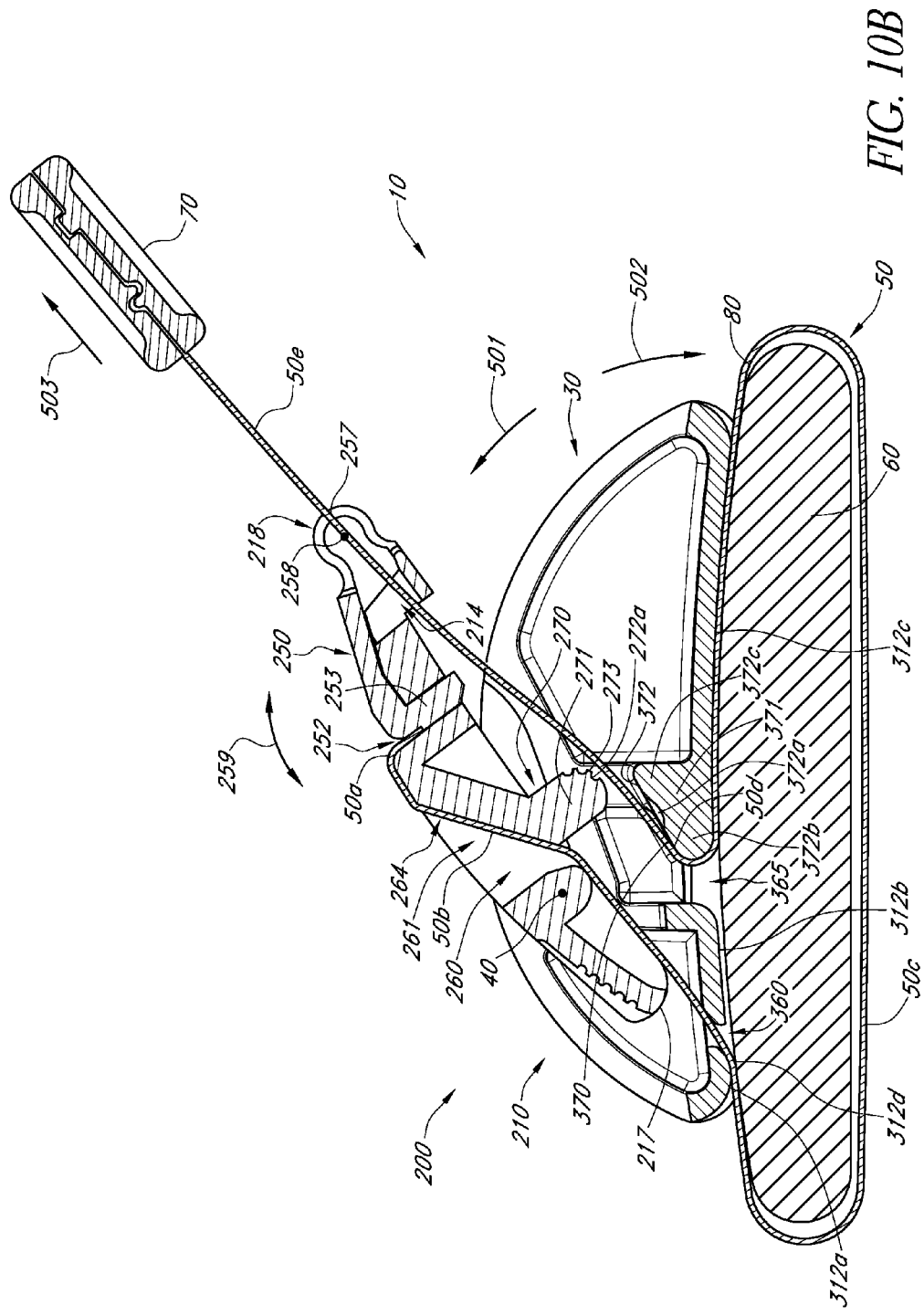

First latch member 20 can comprise a band attachment portion configured to secure a portion of a band to latch member 20, such as the band portion 50*a* described further herein and shown, e.g., in FIGS. 2, 10A and 10B. Referring to FIGS. 2-4 and 10A-10B, the band portion 50*a* can be secured to latch member 20 so that when tension is applied to the band 50, the band 50 will pull and rotate latch member 20 towards latch member 30, as described further herein. The band portion 50*a* can be secured to first latch member 20 in any of many ways. In an embodiment, an end of the attached band portion can be wrapped and secured around a pin or other structure that spans some, most, or all of the width of body 210, and, in some embodiments, between sidewalls 230 (not shown). In the exemplary illustrated embodiment, first latch member 20 comprises a band attachment portion 250 onto which a band portion 50*a* can be secured. The band attachment portion 250 can be positioned anywhere on body 210, preferably giving due consideration to the goal of causing the attached band portion 50*a* to pull and rotate latch member 20 towards latch member 30 when tension is applied to the band 50. The band attachment portion 250 can be positioned on, extend from, or be attached to any of many different portions of the upper side 211 or lower side 212 of body 210. In some embodiments, the band attachment portion 250 can be positioned on upper side 211 and proximate to an opening, or channel 260 extending through body 210. A portion of the band 50 can be attached to attachment portion 250 in any of many ways, such as with clamps, adhesives, thermal, chemical, or ultrasonic bonding, mechanical fasteners, and other methods and structures known in the art Channel 260 can have many different shapes and sizes, such as an opening or slot that spans some, most, or all of the width of body 210, sized and shaped to allow a portion of band 50 to extend from band attachment portion 250 and through body 210. Channel 260 can comprise tapered (e.g., curved or angled) edges or sidewalls, or stepped or radiused shoulders, to guide a portion of band 50 into or through channel 260, or to reduce friction and snagging between the band and channel 260 (see, e.g., FIGS. 5 and 6). Channel 260 can extend through body 210 proximally, or preferably, distally relative to pivot axis 40. Channel 260 can be curved or oriented at many angles relative to body 210 to guide, or change the direction of the band routing through body 210. Without limitation, channel 260 can be curved or oriented at an angle, to advance a portion of a band either distally, or in a preferred embodiment, proximally (FIGS. 5, 6, 10A and 10B) as a portion of the band is extended through body 210 from the upper side 211 to the lower side 212.

Body 210 can comprise a clamping structure 270 (e.g., FIGS. 4-6) with one or more surfaces that can engage with a portion of second latch member 30 to clamp a portion of a band, as described further herein (e.g., FIGS. 7-10B). Clamping structure 270 can be positioned along body 210 proximally, or preferably, distally to pivot axis 40 and/or channel 260. In preferred embodiments, clamping structure 270 is positioned distally relative to channel 260, wherein channel 260 can be positioned distally relative to pivot axis 40. Channel 260 can extend through body 210 between pivot axis 40 and the clamping structure 270.

Clamping structure 270 can comprise any of many different structural configurations attached to body 210. Clamping structure 270 can be either integrally formed with, or alternatively separately formed from, body 210. A separately formed clamping structure 270 can be attached to body 210 using, e.g., threads, mechanical fasteners, tabs, snap-fit, or other known structures and methods. Clamping structure 270 can be removable from body 210 to allow clamping structure 270 to be replaced due to wear or to accommodate various types of bands. Clamping structure 270 can be recessed into, protrude outwardly from, or be substantially flush with or proximate to any of many portions of body 210, and preferably, lower side 212. Clamping structure 270 can comprise a member 271 that spans some, most, or all of the width of body 210, and away from lower side 212. Member 271 can extend from lower side 212 at many different angles relative to body 210, depending on the routing of a band through latch 10. In a preferred embodiment, member 271 is approximately orthogonal to body 210.

Clamping structure 270 can comprise a clamping surface 272 configured to engage with a clamping surface on second latch member 30 and clamp a portion of a band, as described further herein (FIGS. 7-10B). Clamping surface 272 can comprise any of many different structures and/or materials to increase its efficiency in clamping a portion of a band, including any of the configurations described above for the handling portions of closure latch 10. In some embodiments, clamping surface 272 can include one or more ribs 273 that span some, most, or all of its thickness or preferably its width. Clamping surface 272 can be substantially flat or curved, and/or can be angled relative to member 271 and/or latch member 20. In the exemplary illustrated embodiment, surface 272 is substantially flat, and is angled upwardly towards a distal end 218 of latch member 20, to guide a portion of a band towards the distal end 218 of latch member 20.

Figure 4A:
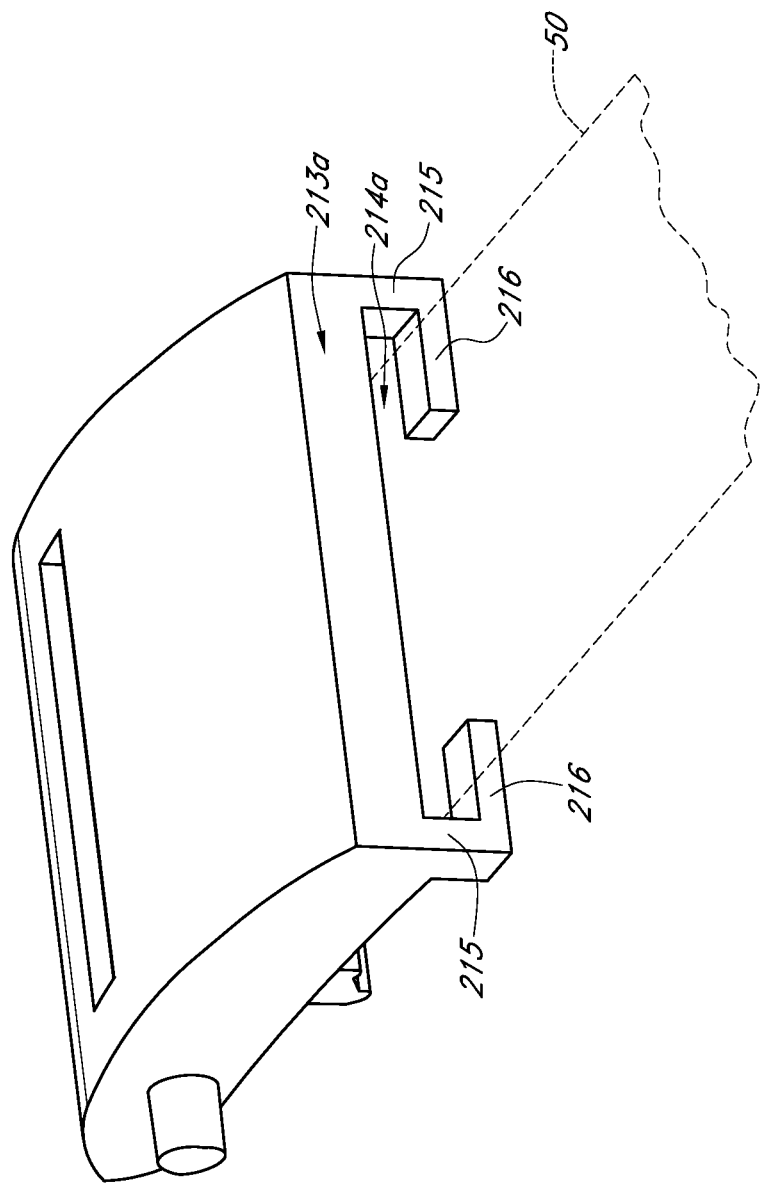
FIG. 4A shows an embodiment of a guide portion of a latch member.

Closure latch 10 can comprise one or more guides configured to guide a portion of a band relative to latch members 20 and/or 30. Such guides may prevent the end of the band from folding or tangling within closure latch 10. In the exemplary embodiment of FIGS. 3 and 4, body 210 can comprise a guide portion 213 with a guide 214 extending therethrough. In some embodiments, the guide portion 213 and guide 214 can be positioned proximate to the distal end 218 of body 210. Guide 214 can guide a portion of a band towards the distal end 218 of body 210, and away from closure latch 10. Guide 214 may improve the ease with which a user may operate latch 10, e.g., while moving latch member 20 relative to second latch member 30. In some embodiments, guide portion 213 and/or guide 214 can allow a user to move latch member 20 relative to second latch member 30, by pulling on a portion of band 50 (e.g., portion 50e), to apply a lateral force to the distal end 218 of first latch member 20 proximate to guide portion 213, as described further herein (see, e.g., FIGS. 10A and 10B). In a preferred embodiment, guide portion 213 and/or guide 214 can allow a user to move latch member 20 relative to second latch member 30 (e.g., to clamp and/or unclamp closure latch 10) by grasping a portion of band 50 with a single hand. In a further preferred embodiment, guide portion 213 and/or guide 214 can allow a user to move latch member 20 relative to second latch member 30 (e.g., clamp and/or unclamp closure latch 10) by grasping a portion of band 50 with a single hand, and without grasping a portion of closure latch 10. Guide portion 213 and guide 214 can be oriented at various angles relative to each other, and relative to the remainder of body 210. In the exemplary illustrated embodiment, guide portion 213 extends approximately orthogonal to body 210, and guide 214 extends approximately parallel to body 210. It will be understood that although guide 214 is shown in FIGS. 3 and 4 as an opening, slot, or channel that may enclose a band extending therethrough, guide 214 can comprise a structure that guides a band without enclosing or surrounding the band. FIG. 4A illustrates an embodiment of a guide portion 213a that can comprise a guide 214a with opposing members 215 that guide the edges of the band 50, and optional support members or lips 216 that extend from the ends of members 215, to partially but not fully wrap around and support a portion of the flat face of the band 50. It will be understood that although guide portions 213 and 213a, guides 214 and 214a, opposing members 215, and lips 216 are shown substantially flat, or straight, in some embodiments these can be curved to guide various-shaped bands.

Figure 5:
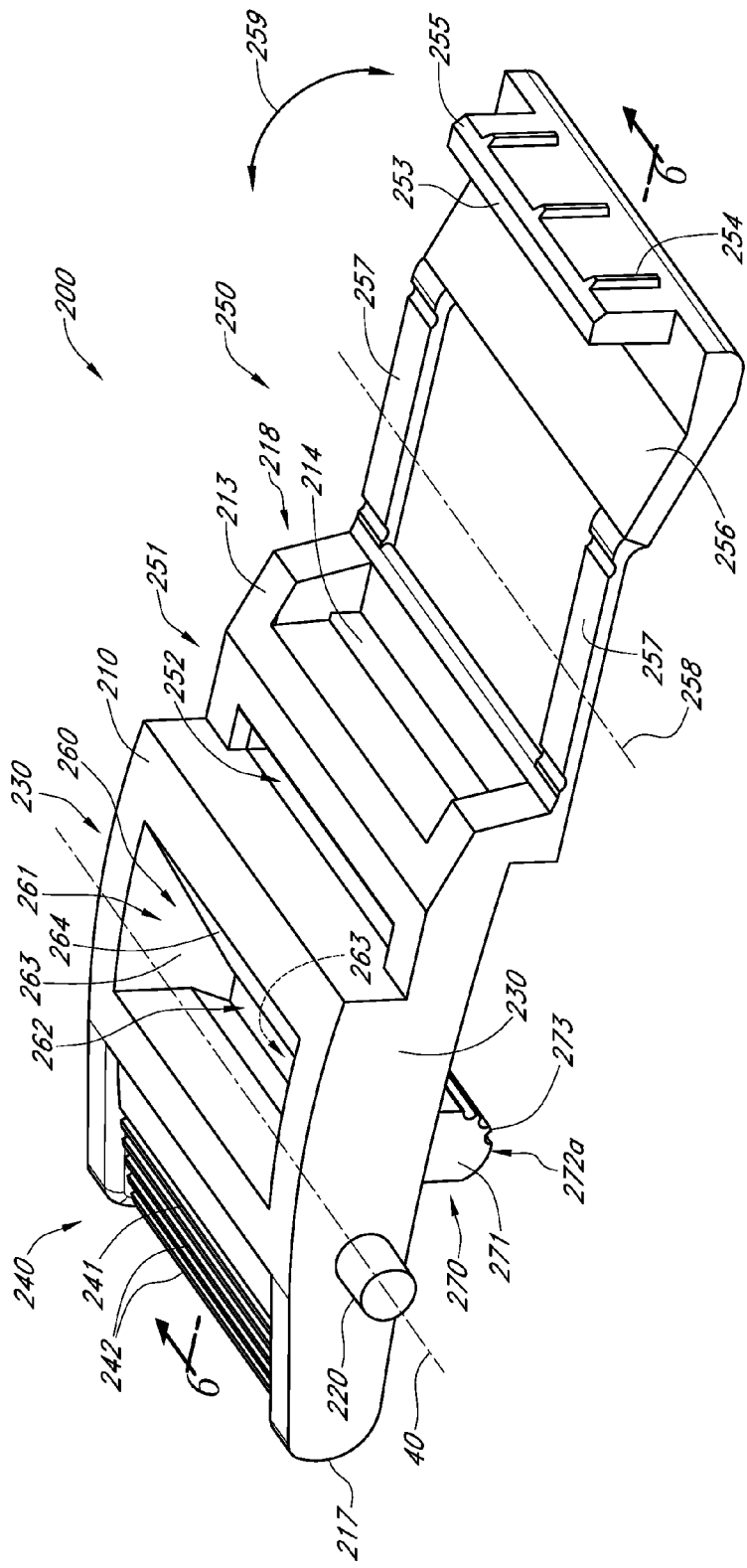
FIG. 5 shows a rear perspective view of an embodiment of a first latch member.
Figure 6:
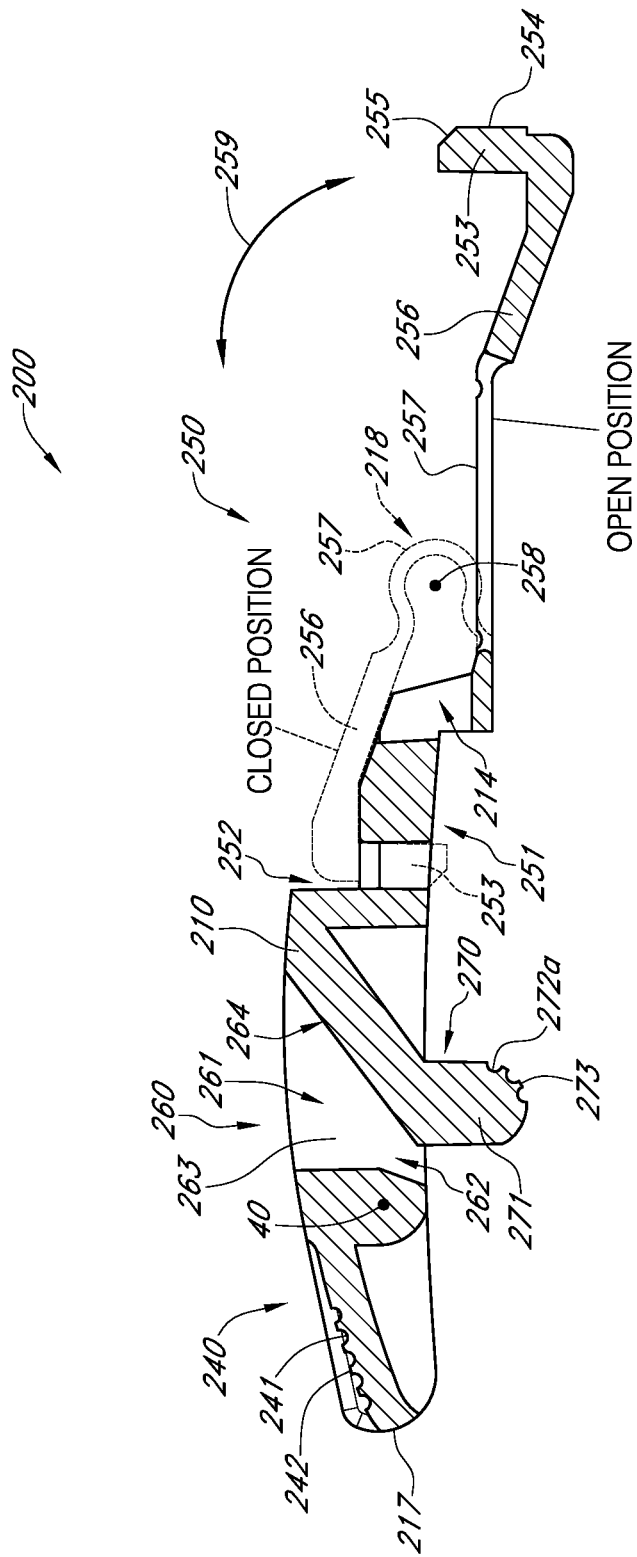
FIG. 6 shows a cross-sectional view of the embodiment of a first latch member taken along line 6-6 of FIG. 5.

FIG. 5 shows a rear perspective view of an embodiment of a first latch member 200. FIG. 6 shows a cross-sectional view of the first latch member 200 taken along line 6-6 of FIG. 5. Many of the components in first latch member 200 are substantially similar to the components of the first latch member 20 shown in FIGS. 1-4, and function similarly to the manner described herein for first latch member 20. One difference between the illustrated first latch member 200 and the first latch member 20 is that the first latch member 200 is illustrated, for exemplary purposes only, with a front handling portion 240 comprising a surface 241 tapered downwardly relative to sidewalls 230 and the remainder of body 210, and with ribs 241, as described above. Another difference between first latch member 200 and first latch member 20 is that the first latch member 200 is illustrated, for exemplary purposes only, with a curved clamping surface 272a that is configured to engage with a recession 372a in second latch member 30 (see FIGS. 7, 8, 10A and 10B).

Channel 260 is also illustrated, for exemplary purposes only, as comprising one or more tapered inner portions, such as tapered sidewalls 261, positioned on opposing inner lateral sides of channel 260, to guide a band along the band's width when extended through channel 260. Channel 260 can comprise a tapered band support 264, positioned on a proximal, or preferably, distal wall of channel 260, to guide a band when extended through channel 260. As such, channel 260 can be configured such that an opening 261 at a first end of channel 260, and an opening 262 at an opposed second end of channel 260 can have different sizes and shapes, to guide a band through channel 260 and body 210. Tapered band support 264 can be configured to be substantially aligned with a channel 360 in second latch member 30, as described further herein (FIGS. 7-10B).

First latch member 200 is illustrated, for exemplary purposes only, with a band attachment portion 250 comprising a band attachment portion body 251 connected to, and preferably extending distally from, body 210. In some embodiments, band attachment portion body 251 can comprise guide portion 213 and guide 214 positioned at the distal end of body 251. Band attachment portion body 251 can comprise an opening 252 configured to receive a portion of a band and a portion of a band attachment member 253, wherein the band attachment member 253 can clamp or hold the portion of the band within opening 252 when both the band attachment member 253 and the portion of the band are inserted into the opening 252 (see, e.g., FIGS. 10A-10B). In the illustrated embodiment, the opening 252 is sized and shaped to form a slot, although it will be understood that opening 252 can be sized and shaped to receive and hold various types of bands, straps, and the like. Opening 252 can extend partially into or through body 251 and can span some, most, or all of the width of body 251.

Band attachment member 253 can comprise any of many different configurations that can be inserted into opening 252 to hold a portion of a band within opening 252. Band attachment member 253 can have a tapered shape to provide a frictional fit between member 253, opening 252, and a portion of the band. In the illustrated embodiment, attachment member 253 can comprise an approximately rectangular prism shape, with optional ribs 254 extending along and from member 253 to form a frictional fit between member 253, opening 252 and a portion of the band.

Band attachment member 253 can be a separate piece from attachment portion 250, or can be integrally formed therewith. Band attachment member 253 can comprise an optional tapered portion 255 at its distal end so that opening 252 can more easily receive member 253 and a portion of a band. In an embodiment, band attachment member 253 can be attached to body 251 with one or more support members 257 positioned between body 251 and attachment member 253. In another embodiment, attachment portion 250 can comprise an optional handling portion 256 attached to band attachment member 253, which can comprise structure and functionality substantially similar to the other handling portions described herein, and which can assist a user in inserting band attachment member 253 into opening 252. Support members 257 can be sufficiently flexible to allow them to flex around a support member axis 258 when attachment member 253 is moved between an open position (e.g., unclamped position, shown in FIG. 5 and in solid lines in FIG. 6) and a closed position (e.g., clamped position, shown in phantom lines in FIG. 6) in the direction shown by directional arrows 259, e.g. inserted into opening 252.

Figure 7:
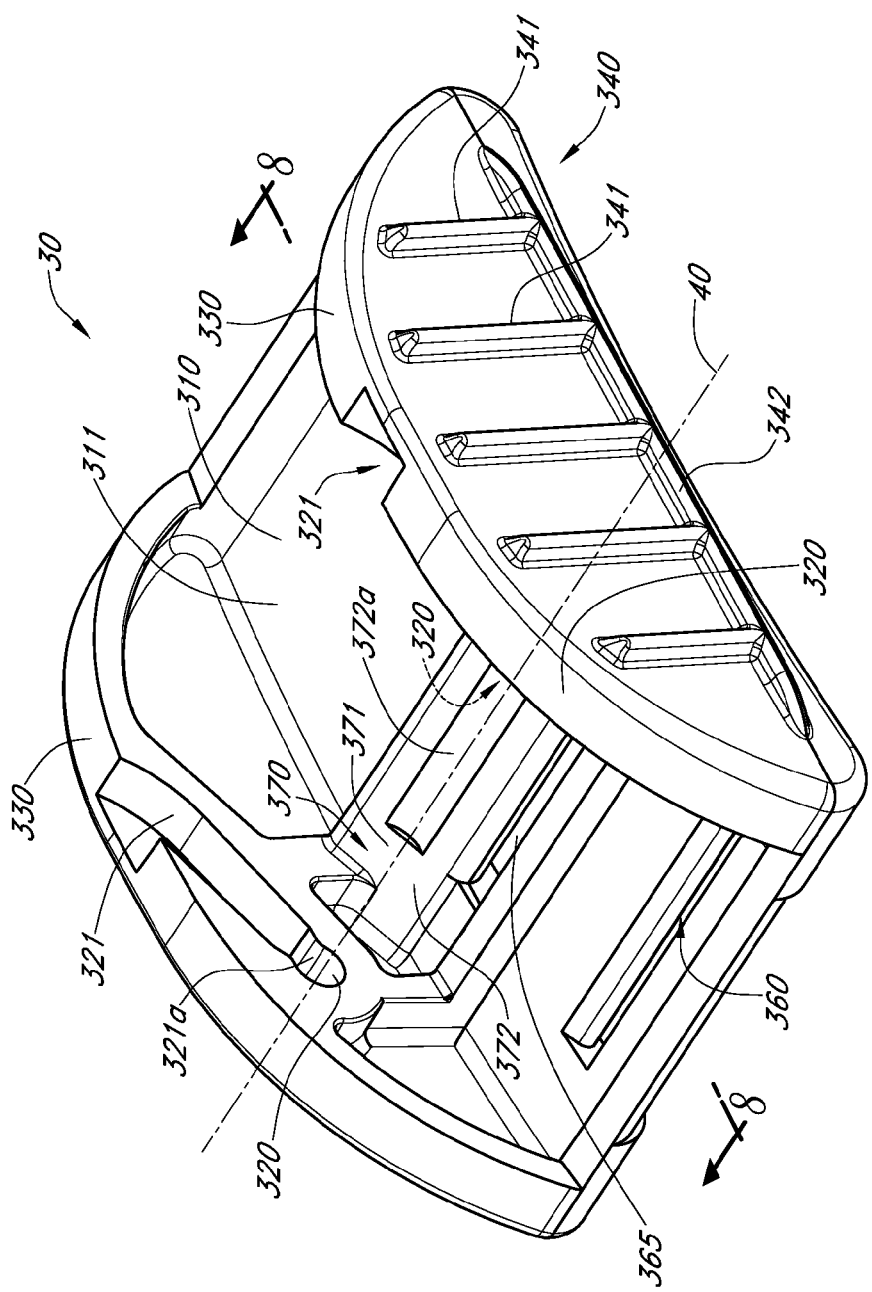
FIG. 7 shows a front and right side perspective view of an embodiment of a second latch member.
Figure 8:
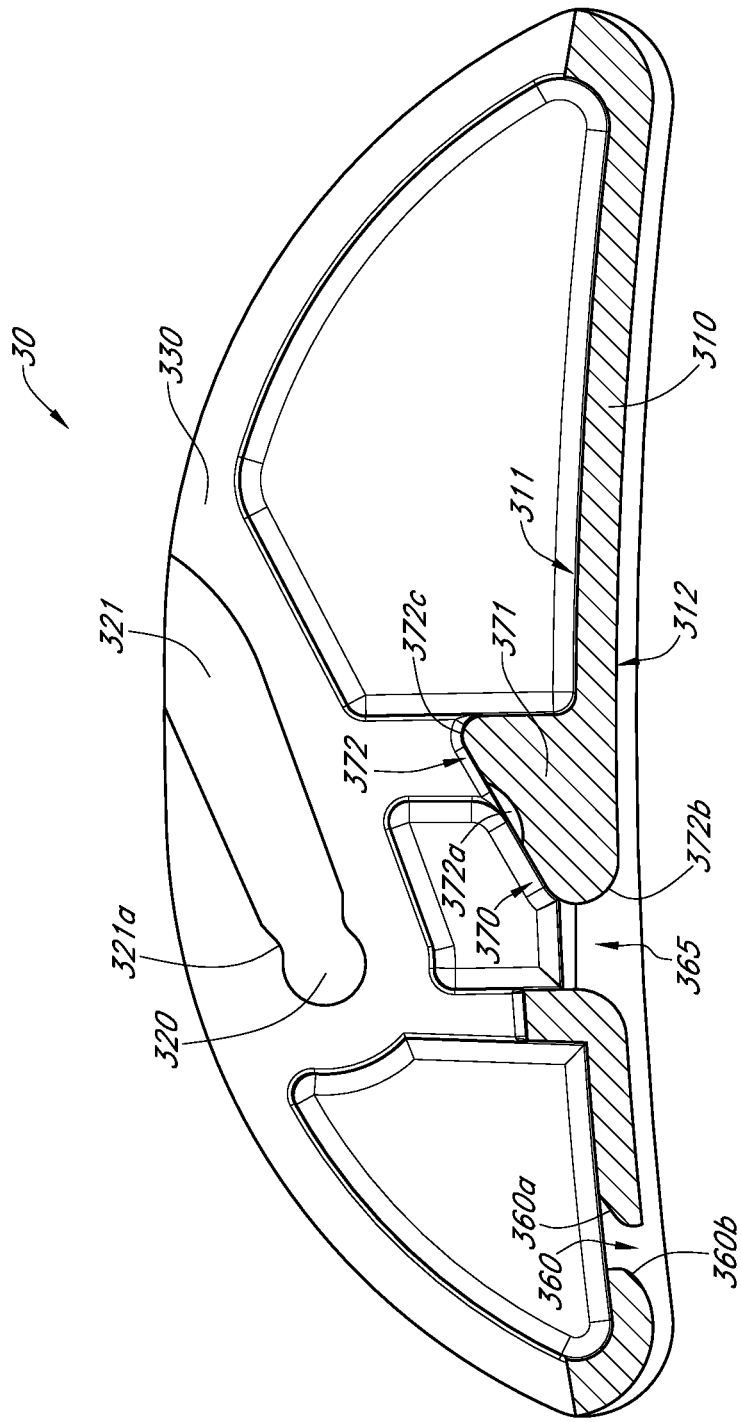
FIG. 8 shows a side cross-sectional view of an embodiment of a second latch member taken along line 8-8 of FIG. 7.

FIG. 7 shows a front and right side perspective view of an embodiment of the second latch member 30 of the closure latch 10 of FIGS. 1 and 2. FIG. 8 shows a side cross-sectional view of the second latch member 30 taken along line 8-8 of FIG. 7. Second latch member 30 can comprise a base 310 configured to pivot relative to first latch member 20 about the pivot axis 40, as described above (FIGS. 1 and 2). Base 310 can comprise an upper-side 311 that generally faces towards first latch member 20, and a lower side 312 that generally faces away from first latch member 20, when second latch member 30 is engaged with first latch member 20. Base 310 can comprise any of many shapes, such as an approximately rectangular, ovular, trapezoidal, or other prismatic shape. In a preferred embodiment, base 310 comprises an approximately rectangular-shape, with a pair of opposing sidewalls 330 attached approximately along the outer edges of base 310 and extending away therefrom. Base 310 can comprise a substantially flat or curved top and/or bottom surfaces, and in the exemplary illustrated embodiment, a convex top surface and/or concave bottom surface. Sidewalls 330 can comprise an approximately rectangular, elliptical, or circular shape, although in a preferred embodiment, sidewalls 330 are a curved shape extending from base 310, and more preferably, a substantially arch-like, or semicircular shape.

Second latch member 30 can comprise one or more rotational members 320 configured to rotationally engage with rotational members 220 of first latch member 20, 200 (FIGS. 3-5) and allow second latch member 30 to pivot about pivot axis 40 relative to first member 20, 200 (see, e.g., FIGS. 1-3, 10A-10B). The rotational member 320 can comprise any of many rotational structures described herein for rotational member 220, but configured to rotationally engage with, receive, and/or be received by rotational member 220. Rotational member 320 can comprise a pair of curved, partially circular recesses extending laterally completely through, or partially into the side of each sidewall 330. Each rotational member 320 can be connected to a groove 321, extending laterally completely through or partially into sidewall 330. Groove 321 can also extend longitudinally along a portion of sidewall 330. In a preferred embodiment, groove 321 extends longitudinally from an outer edge of sidewall 330 to an inner portion of sidewall 330, preferably towards base 310, to allow rotational member 220 to be received by groove 321 and rotational member 320, and thus allow first latch member 20 to engage, rotationally engage, and/or removably engage with second latch member 30 (see, e.g., FIGS. 1 and 2). Groove 321 can comprise a shoulder 321a between groove 321 and rotational member 320, to retain rotational member 220 within member 320. Groove 321, rotational member 220 and rotational member 320 can simplify the assembly of closure latch 10. It will be understood that rotational members 320 and grooves 321 (and thus, pivot axis 40) can be positioned anywhere along the length of sidewalls 330. It will also be understood that the configuration of rotational member 220 and rotational member 320 can be reversed relative to first latch member 20 and second latch member 30, such that member 220 is positioned on latch member 30, and member 320 is positioned on member 20.

As described above, second latch member 30 can include one or more handling portions to allow a user to easily grasp and move second latch member 30 relative to first latch member 20. In an embodiment, second latch member 30 can comprise a handling portion 340 configured on sidewalls 330. Handling portion 340 can comprise one or more ribs 341 and/or elongated members 342, extending from an outer portion of sidewall 330. It will be understood that handling portion 340 can be positioned elsewhere on second latch member 30, and can comprise other structure and functionality substantially similar to the other handling portions described herein.

Second latch member 30 can comprise one or more openings, channels, or slots extending through base 310 through which a portion of a band can extend. In a preferred embodiment, a first channel 360 can extend completely through base 310, to allow a band to extend through base 310. First channel 360 can comprise any of the shapes, sizes and configurations of, and can function substantially similarly to, channel 260 described herein. In a preferred embodiment, first channel 360 can comprise one or more surfaces that can be tapered, e.g. angled (e.g., surface 360a), or curved (e.g., surface 360b) in a direction corresponding to the direction of the passage of a portion of a band through channel 360, and in some embodiments, towards the proximal end of second member 30. Channel 360 can be positioned proximate to edge, such as a proximal edge, of base 310, to stabilize closure latch 10 during its use, e.g., to prevent closure latch 10 from twisting while it is being used to secure a band around an object.

In some embodiments, base 310 can comprise a second channel 365 extending through base 310, to allow a band to extend through base 310. Second channel 365 can be configured to guide a same or different portion of the band extending through base 310 relative to the portion of the band extending through first channel 360. Second channel 365 can comprise any of the shapes, sizes and configurations of, and can function substantially similarly to, channels 260 and 360 described herein. In a preferred embodiment, channel 365 can be spaced longitudinally from channel 360, to stabilize closure latch 10 during its use, e.g., when a first portion of a band extends through channel 365, and a different portion of a band extends through channel 360.

Base 310 can comprise a clamping structure 370 configured to engage with a portion of clamping structure 270 of first latch members 20 or 200 to clamp a portion of a band, as described further herein (see FIGS. 3-6, 10A-10B). Clamping structure 370 can be positioned along base 310 proximally, or preferably, distally with respect to pivot axis 40 and/or channels 360 and/or 365. Channel 360 and/or channel 365 can extend through base 310 between pivot axis 40 and the clamping structure 370.

The structure, features, and function of clamping structure 370 can be substantially similar to those described herein for clamping structure 270. A portion of the clamping structure 370, such as one or more clamping surfaces, can be configured to engage with, and in some embodiments, oppose a portion of clamping structure 270. Clamping structure 370 can be formed integrally or separately relative to base 310. A separately formed clamping structure 370 can be attached to base 310 with, e.g., threads, mechanical fasteners, tabs, snap-fit, or other known structures and methods. Clamping structure 370 can be removable from base 310 to allow clamping structure 370 to be replaced due to wear or to accommodate various sizes or types of bands. Clamping structure 370 can be recessed into, protrude outwardly from, or be substantially flush with or proximate to any of many portions of base 310, and preferably upper side 311. Clamping structure 370 can comprise a member 371 that spans some, most, or all of the width of base 310, and away from upper side 311. Member 371 can extend from upper side 212 at many different angles relative to base 310, depending on the routing of a band through latch 10, and the angle of the opposed clamping structure 270 on body 210. In a preferred embodiment, member 371 extends protrudes upwardly from base 310.

Clamping structure 370 can comprise a clamping surface 372 configured to engage with, and in some embodiments, oppose, clamping surface 272 on first latch member 20 and clamp a portion of a band, as described further herein. The structure, features, and function of clamping surface 372 can be substantially similar to those described herein for clamping surface 272. In some embodiments, clamping surfaces 272 and 372 can comprise paired structures to improve the engagement between clamping surfaces 372 and 272, such as conforming, meshing or interlocking ribs, teeth, grooves, pins, and the like. In the exemplary illustrated embodiment, clamping surface 372 can include a recession 372a configured to receive and conform to a corresponding portion of clamping surface 272. Recession 372a can comprise many different shapes, but is shown for exemplary purposes only as a substantially concave recession extending partially into clamping surface 372 and partially across the width of member 371.

Clamping structures 270 and/or 370 (including clamping surfaces 272 and/or 372) can comprise tapered (e.g., curved or angled), stepped or radiused edges, sidewalls, surfaces or shoulders, to guide a portion of a band along and between clamping structures 270 and 370 (when in an unclamped, or unengaged position) and/or to reduce friction and snagging between a portion of the band and clamping structures 270 and/or 370. In the exemplary illustrative embodiment, clamping surface 372 is angled to guide a portion of a band upwardly towards a distal portion of base 310. Clamping surface 372 can also comprise curved portions 372b and 372c at its proximal and distal edges, respectively, to assist in guiding a band around the proximal and distal edges of clamping structure 370.

Figure 9:
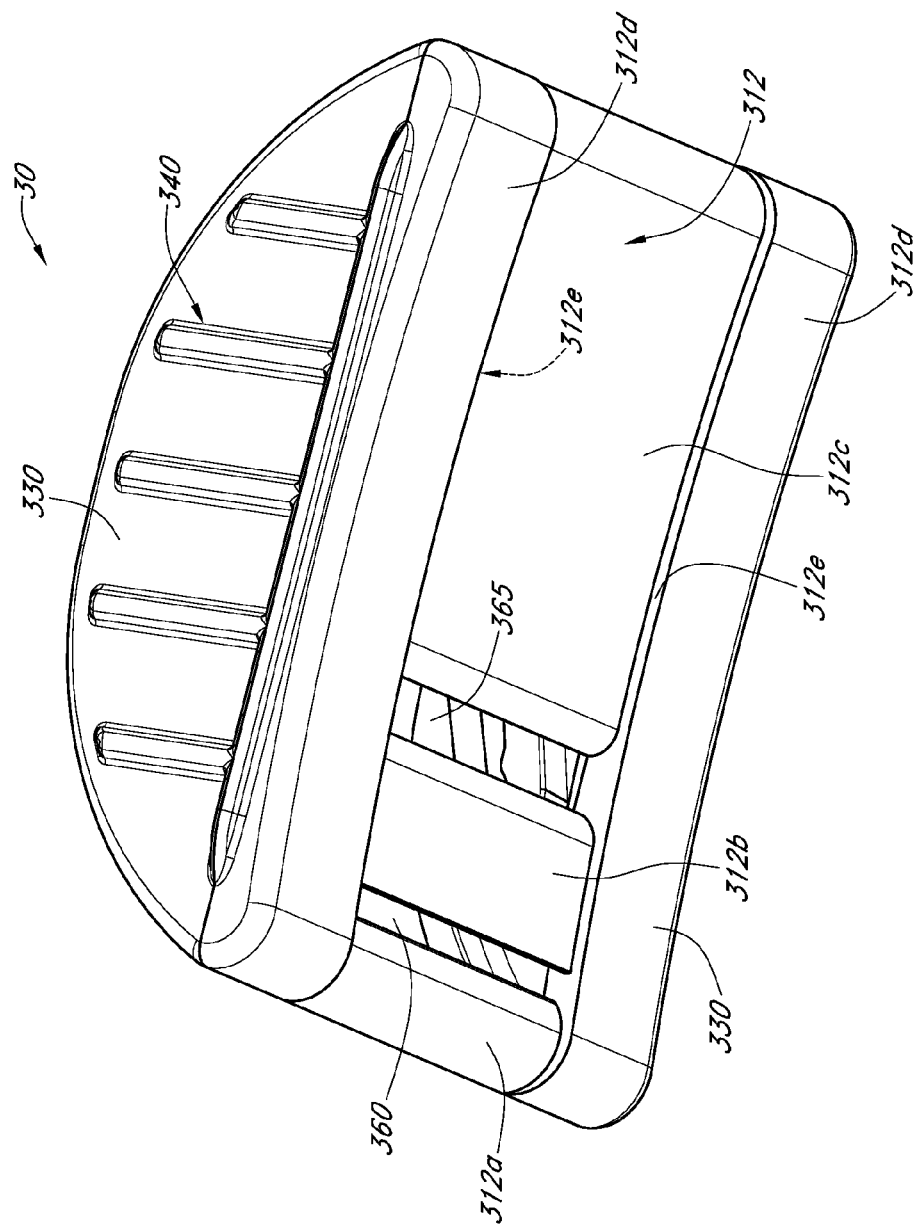
FIG. 9 illustrates a bottom side perspective view of an embodiment of a second latch member.

FIG. 9 illustrates a bottom side perspective view of an embodiment of second latch member 30. In the exemplary embodiment, lower side 312 can comprise one or more stepped or recessed portions, to guide a portion of a band extending along the lower surface of lower side 312. In the illustrative embodiment, recessed portions 312a-312c can extend laterally between a paired of outer, or as shown, guide portions 312d (e.g., shoulders), with stepped or radiused shoulders 312e at the transition between recessed portions 312a-312c and guide portions 312d. It will be understood that although the illustrated embodiment shows three recessed portions 312a-c, any of these or other portions of lower side 312 can be recessed, protrude, or be flush with the outer portions 312d. In some embodiments, the proximal and distal portion of sections 312a and 312c, respectively, can be curved to further assist in guiding a band along lower side 312.

The various latch member embodiments described herein can comprise any of many different materials, such as plastic or metal, and can comprise more than one material, such as a composite, or a metal coated with rubber, plastic, or foam. The latch members can comprise the same or can comprise different materials relative to each other. The latch members can be thermally, chemically or mechanically treated to provide, or can comprise any material that provides, increased durability, flexibility, moisture absorption or adsorption, and/or chemical resistance. The latch members can comprise a material of any color, and can comprise a substantially transparent, opaque, or translucent material, or any combination thereof. The latch members may be any of myriad compositions suitable for short-term or long-term contact with a user's skin. Suitable methods for manufacturing the latch members include injection molding, casting, machining, and other construction techniques that are well known in the art.

FIGS. 10A and 10B illustrate a method of using an embodiment of closure latch 10 to clamp and unclamp, respectively, a portion of band 50, and the routing of band 50 through closure latch 10. It will be understood that substantially similar methods can be used to clamp and unclamp a band with the various other embodiments of closure latches described herein. As used in reference to FIGS. 10A and 10B, "user" can refer to either or both a user and manufacturer of closure latch 10.

The user first engages first latch member 200 and second latch member 30 to each other such that the first and second latch members 200 and 30 can pivot relative to each other about pivot axis 40. In some embodiments, this step comprises inserting a first pair of rotational members 220 of the first latch member 200, or in some embodiments, the second latch member, into a pair of opposed slots 321 on the other of the first latch member 200 or the second latch member 30, and sliding the first pair of rotational members 220 to engage with a second pair of rotational members 320 positioned at an end of said slots 321 (see, e.g., FIGS. 1 and 3-9).

Referring again to FIGS. 10A and 10B, the user secures a first band portion 50a of band 50, preferably a proximal end of band 50, to the first latch member 200 using any of the structures of band attachment portion 250 and any of the attachment methods described herein. In the exemplary embodiment, the band attachment member 253 can be inserted into the opening 252 with first band portion 50a to form a frictional fit between member 253, opening 252 and band portion 50a, securing the first band portion 50a to the band attachment portion 250. In some embodiments, the band attachment member 253 can be inserted into the opening 252 by moving member 253 and flexing support members 257 around axis 258 in the direction shown by directional arrows 259. In some embodiments, the first band portion 50a can be extended to wrap around a distal edge of body 210 or at least past the edge of opening 261 of channel 260 (see FIGS. 6, 10A and 10B).

Referring again to FIGS. 10A and 10B, the user extends a second band portion 50b of band 50 from the edge of opening 261, through channel 260 of first latch member 200, and through opening 360 in second latch member 30. In some embodiments, this step can comprise extending the second band portion 50b between the pivot axis 40 and the clamping structure 270. In some embodiments, this step can comprise substantially aligning the tapered band support 264 with opening 360 in the second latch member 30, and preferably, extending second band portion 50b along the tapered band support 264 from the first band section 50a to opening 360. In some embodiments, second band portion 50b can be extended from opening 260 through opening 365. In some embodiments, opening 260 can be substantially aligned with opening 365.

The user extends a third band portion 50c to form a loop 80 attached to closure latch 10, extending a first end of the loop 80 proximate to the opening 360 (or in some embodiments, opening 365), around an object 60, and to a second end proximate to opening 365. In an alternative embodiment, a loop 80 is not formed, and third band portion 50c can comprise two separate segments, one segment with an end proximate to opening 360, the other with an end proximate to opening 365; both segments with an opposed free end (not shown) that may be secured to the object 60. In a preferred embodiment, third band portion 50c is guided along recessed portions 312a, 312b, and/or 312c, between guide portions 312d.

The user extends a fourth band portion 50d through opening 365, and between clamping members 271 and 371, and in some embodiments, along surface 372. In a preferred embodiment, the fourth band portion 50d can be extended around a curved portion 372b of clamping member 371, to reduce friction between the band 50 and the closure latch 10 as the band 50 is placed under tension prior to clamping.

The user extends a fifth band portion 50e, which preferably comprises the remaining distal portion of band 50, from between the clamping members 271 and 371, and through opening 214. In some embodiments, this step comprises extending fifth band portion 50e between the members 257 of the band attachment portion 250. In some embodiments, the clamping surface 372 is configured to be substantially aligned with opening 214 such that fourth and fifth band portions 50d and 50e form a substantially straight line when fourth band portion 50d extends between clamping members 271 and 371 and along surface 372, and when fifth band portion 50e extends from clamping members 271 and 371 through opening 214. The user can attach clasp 70 around the free, distal end of fifth band portion 50e extending from closure latch 10, to allow the user to easily grasp the band 50 during use, and prevent the fifth band portion 50e from slipping back through the above described band routing within closure latch 10.

Once the band 50 has been routed through the closure latch 10 as described above, the user inserts an object 60 into the loop 80 formed by band portion 50c. In the alternative embodiment wherein band portion 50c comprises two band segments, during this step, the free end of each band segment can be attached to the object 60, or any intermediate structure (e.g., a medical barrier). Next, the user moves the closure latch 10 to an open position by pivoting first latch member 200 relative to second latch member 30 about axis 40 in the direction shown by arrow 501, and/or by pivoting second latch member 30 relative to first latch member 200 in the direction shown by arrow 502 (FIG. 10B). In some embodiments, the user moves closure latch 10 by grasping and moving the distal end 218 of first latch member 200 relative to second latch member 30. In some embodiments, the user moves closure latch 10 to an open position by pulling on band portion 50e in direction 501 (e.g., against guide portion 213 and/or guide 214), which causes band portion 50e to pull, and thus move, the distal end 218 (e.g., guide portion 213 and/or guide 214) of first latch member 200 in direction 501 relative to second latch member 30. In a preferred embodiment, the user can move latch member 20 to an open, or unclamped, position relative to second latch member 30 with a single hand grasping band portion 50e, and in a further preferred embodiment, without grasping a portion of closure latch 10. In another preferred embodiment, the user can move the latch member 20 to an open position by pressing the proximal end 217 vertically down towards member 30. Next, the user pulls the distal end of the band portion 50e in the direction shown by directional arrow 503, to remove any slack in the band routing and around object 60.

In some embodiments, when the user moves closure latch 10 to the open position, the user moves first latch member 200 relative to second latch member 30 in direction 501 to a position wherein band portions 50d and 50e form a substantially straight line from the proximal edge 372b of clamping surface 372 and the distal end 218 of first latch member 200. In a further preferred embodiment, the user moves first latch member 200 relative to second latch member 30 in direction 501 to a position wherein there is no substantial contact (e.g., friction or restriction) between the portion of band portion 50d contacting the proximal edge 372b of clamping surface 372 and band portion 50e with closure latch 10. In an even further preferred embodiment, the user moves first latch member 200 relative to second latch member 30 in direction

501 to a position wherein band portions 50*d* and 50*e* form a substantially straight line from opening 365 to the distal end 218 of first latch member 200 (e.g., between the distal end of band portion 50*c* and guide 214). In an even further preferred embodiment, the user moves first latch member 200 relative to second latch member 30 in direction 501 to a position wherein there is no substantial contact (e.g., friction or restriction) between band portions 50*d* and 50*e* with closure latch 10. In effect, embodiments of closure latch 10 can be used with a band 50 comprising substantially straight band portions 50*d* and/or 50*e*, and/or embodiments with reduced contact between band portions 50*d* and 50*e* and closure latch 10. These embodiments of closure latch 10 allow portions of the closure latch 10 (e.g., first latch member 200) to basically freefall into the tightening or closing position, with reduced friction between portions of the latch 10 and the band 50, thus allowing the user to more easily pull the distal end of the band portion 50*e* in the direction shown by directional arrow 503, to remove any slack in the band routing and around object 60. These embodiments can ease the effort with which a user (e.g., a child or a physically challenged or a geriatric user) can apply, open and tighten (e.g., cinch) latch 10 around an object, such as the user's appendage. Once the band 50 is applied around an object, the substantially straight portions of the band 50 and/or the reduced contact between the band and closure latch 10 can reduce the tension required by the user when pulling the distal end of the band to remove the slack in the band around object 60.

Next, the user further pulls the band portion 50*e* to form a desired tension in band 50, and to tighten the loop around object 60. In a preferred embodiment, this step can be performed with a single hand, and in a further preferred embodiment, without removing the user's grasp on band portion 50*e* after the prior step of opening the closure latch 10. The tension in the band 50, and in some embodiments, the tension in the band between band portion 50*a* and 50*d*, applies tension to a portion of the band (e.g., portion 50*b* and/or 50*a*) that is radially offset from pivot axis 40, pulling on attachment portion 250 (see, e.g., FIGS. 10A and 20), and causing latch member 200 to rotate in a clockwise direction about pivot axis 40. Thus the tension between band portion 50*a* and 50*d* causes the band 50 to pull the first latch member 200 and the second latch member 30 towards each other. This in turn causes first latch member 200 to pivot relative to second latch member 30 about axis 40 in the direction shown by arrow 502, and/or causes second latch member 30 to pivot relative to first latch member 200 in the direction shown by arrow 501. This in turn causes closure device 10 to move to a closed position, causing clamping structures 271 and 371 to engage each other and clamp band portion 50*d* (FIG. 10A). Once closure device 10 is in a closed position, tension will remain in the band between the clamped band portion 50*d* and the attached portion 50*a*, even after tension is released from band portion 50*e*, holding the closure device in a closed position. In an embodiment using an elastic band 50, the thickness of band portion 50*e* will increase after tension is released from band portion 50*e*, helping to prevent band portion 50*e* from sliding proximally past clamping structures 271 and 371.

In some embodiments, the user can hold the closure latch 10 in an open position while pulling the band to a desired tension, causing a force pulling first latch member 200 and second latch member 30 towards each other. While holding band 50 at the desired tension, the user can move the closure latch 10 to a closed position by pivoting first latch member 200 relative to second latch member 30 about axis 40 in the direction shown by arrow 502, and/or by pivoting second latch member 30 relative to first latch member 200 in the direction shown by arrow 503, so that clamping structures 271 and 371 engage each other and clamp band portion 50*d* (FIG. 10A). In some embodiments, the user moves closure latch 10 to a closed position by pulling on band portion 50*e* in direction 502 (e.g., against guide portion 213 and/or guide 214), which causes band portion 50*e* to pull, and thus move, the distal end 218 (e.g., guide portion 213 and/or guide 214) of first latch member 200 in direction 502 relative to second latch member 30. In a preferred embodiment, the user can move latch member 20 to a closed or clamped position relative to second latch member 30 with a single hand grasping band portion 50*e*, and in a further preferred embodiment, without grasping a portion of closure latch 10. In some embodiments, this step of moving latch 10 to a closed position can comprise two steps, wherein the user first moves first latch member 200 in direction 502 as described above until clamping structures 271 and/or 371 initially contact band portion 50*d*, and next, the user further moves first latch member 200 in direction 502 until opposed clamping surfaces 272*a*, 372*a* engage. Upon moving latch 10 to a closed position, the user releases the user's grasp on band portion 50*e*, and the tension in band 50 will hold latch 10 in a closed position, as described further herein.

In an alternate embodiment, the closure latch 10 can be moved to a closed position after removing any slack in the band routing and around object 60, and prior to pulling the band portion to a desired tension around object 60. In such an embodiment, portion 50*d* may slide distally between clamping portions 270, 370 while tension is being applied to band portion 50*e*, but portion 50*d* will tend to be secured between clamping portions 270, 370 when tension is released from band portion 50*e*. This is due to the tension in band portion 50*a*, 50*b*, and 50*c* acting to pull the first and second latch members together to increase the clamping force on band portion 50*d*.

The simplicity of closure latch 10 and the band routing described herein allows a user to insert the object into the loop, move the closure latch to an open or unclamped position, tighten the loop to the desired tension around the object, and clamp the band within latch 10, with any, or preferably, all of these steps being performed with a single hand, and even more preferably, without removing the user's grasp from the band. This feature can be beneficial to a user who must use and apply latch 10 without the assistance of a second individual.

Figure 11:
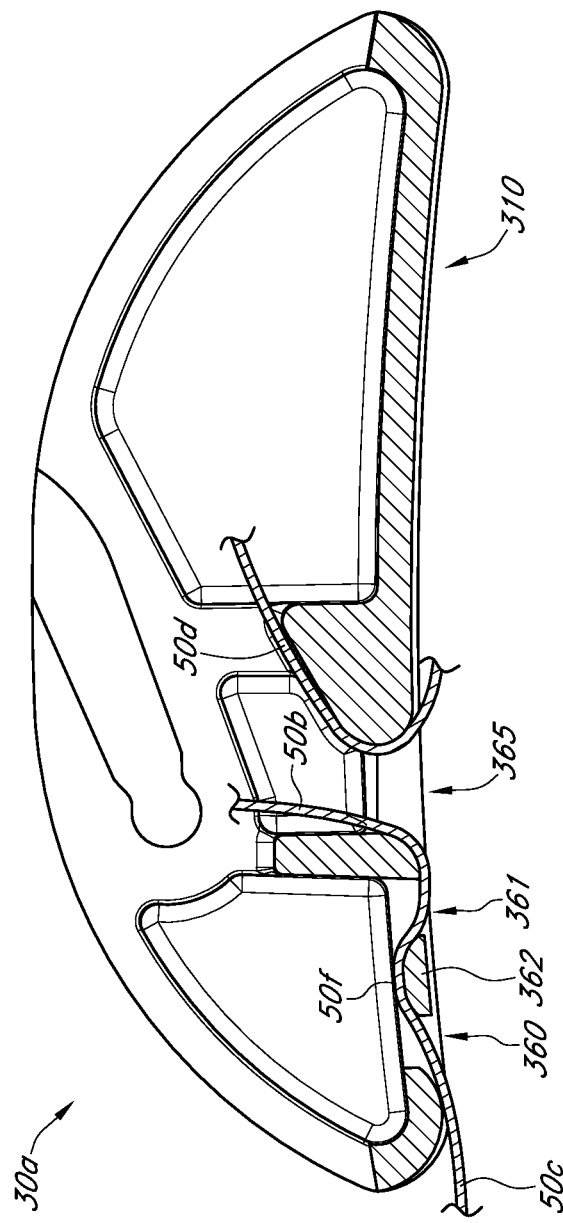
FIG. 11 shows a side cross-sectional view of an embodiment of a second latch member.

FIG. 11 shows a side cross-sectional view of an embodiment of a second latch member 30*a*. The structure and functionality of second latch member 30*a* can be substantially similar to those described herein for second latch member 30. One difference between the second latch member 30*a* and the second latch member 30 is second latch member 30*a* can comprise an opening 361 positioned between openings 365 and 360. A band support member 362 can be configured to span some, most, or all the width of base 310, and between openings 360 and 361. During use, a user extends band portion 50*b* through opening 365. A sixth band portion 50*f*, between and attached to second band portion 50*b* and third band portion 50*c*, can be extended through opening 361, over member 362, and through opening 360. This configuration can provide additional guidance and stabilization to the routing of band 50 through closure latch 10.

Figure 12:
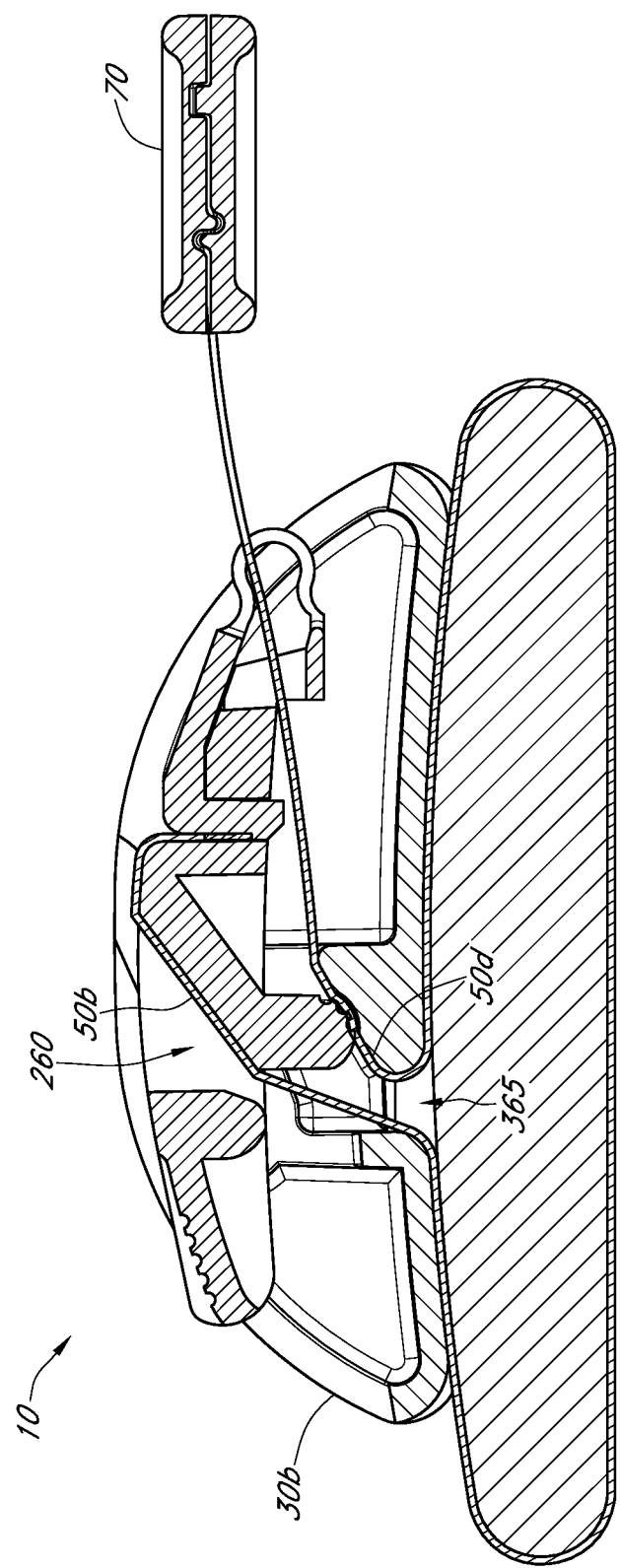
FIG. 12 shows a side cross-sectional view of an embodiment of a closure latch comprising a second latch member.

FIG. 12 shows a side cross-sectional view of an embodiment of a closure latch 10 comprising a second latch member 30*b*. The structure and functionality of second latch member 30*b* can be substantially similar to those described herein for second latch members 30 and 30*a*. One difference between the second latch member 30*b* and the second latch members 30 and 30a is opening 360 has been omitted from second latch member 30b, and opening 365 is substantially aligned with channel 260. In use, both second band portion 50b and fourth band portion 50d extend through opening 365.

Figure 13:
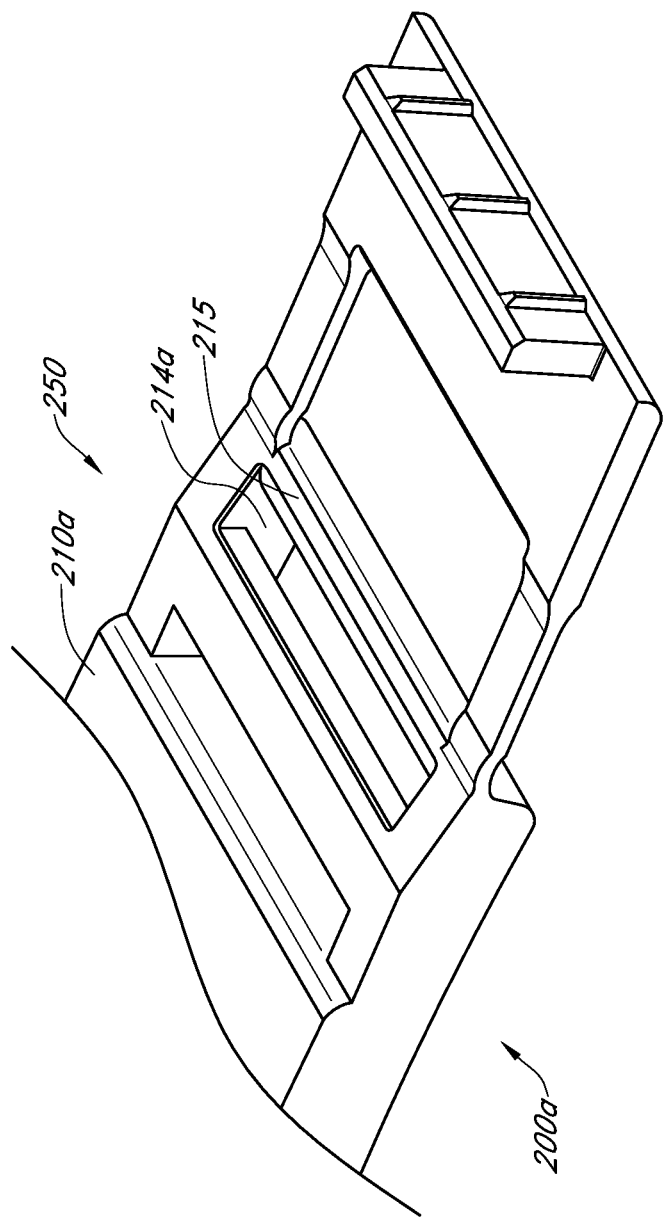
FIG. 13 shows a partial rear perspective view of an embodiment of a first latch member.

FIG. 13 shows a partial rear perspective view of an embodiment of a first latch member 200a. Many of the components in first latch member 200a are substantially similar to the components of the first latch members 20 and 200 shown in FIGS. 1-6, and function similarly to the manner described herein for first latch members 20 and 200. One difference between the illustrated first latch member 200a and the first latch member 200, is that the first latch member 200a is illustrated with a guide 214a configured to guide a band upwardly from the body 210a and a guide edge 215 that is approximately parallel with the body 210a of first latch member 200a. Upwardly facing guide 214a can permit a user to pull the band upwardly relative to first latch member 200a without restriction, and guide edge 215 can provide guidance to a band when the band is pulled substantially parallel to a body 210a of latch member 200a.

Figure 14:
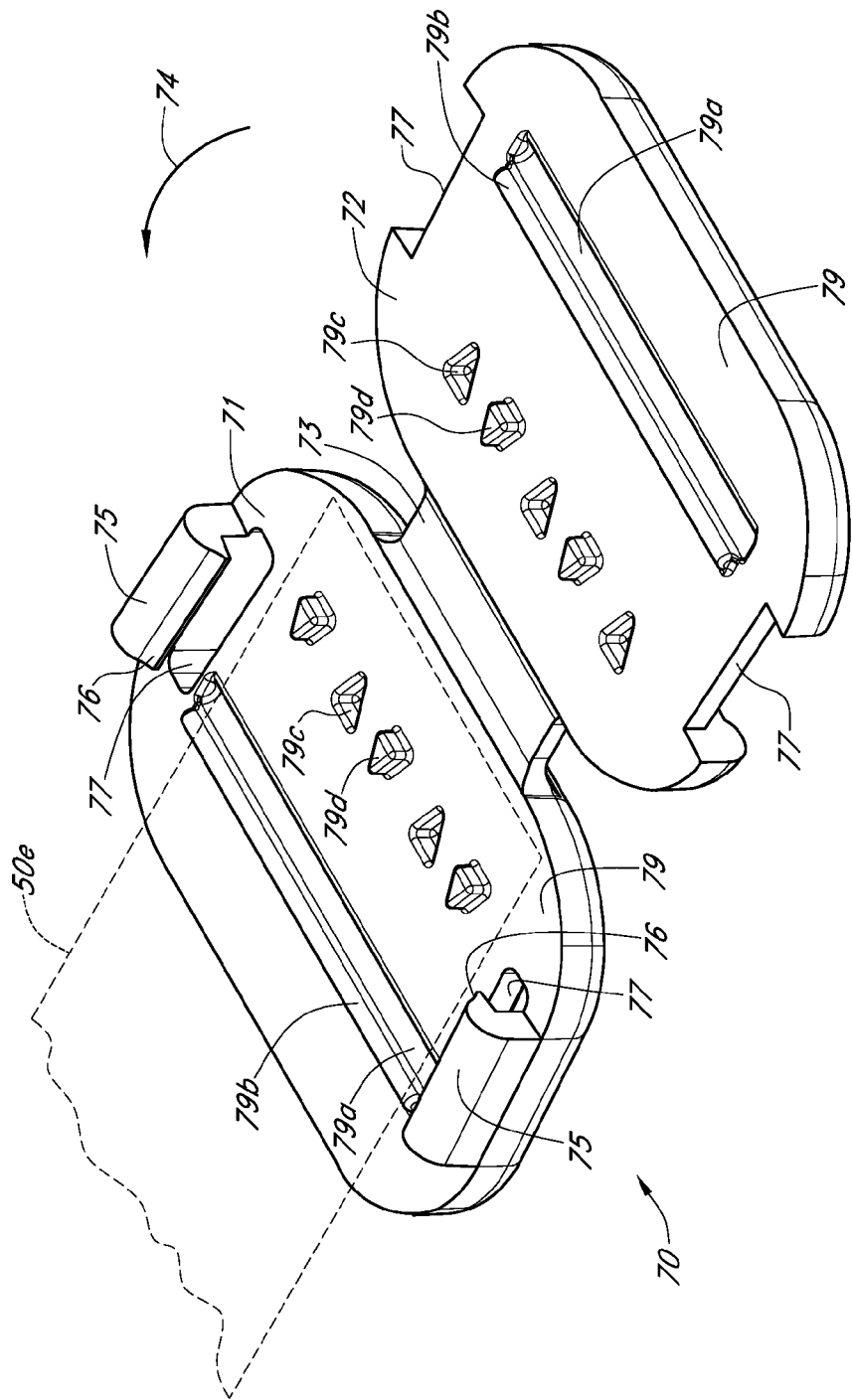
FIGS. 14 and 15 illustrate perspective and top views, respectively, of an embodiment of a clasp.
Figure 15:
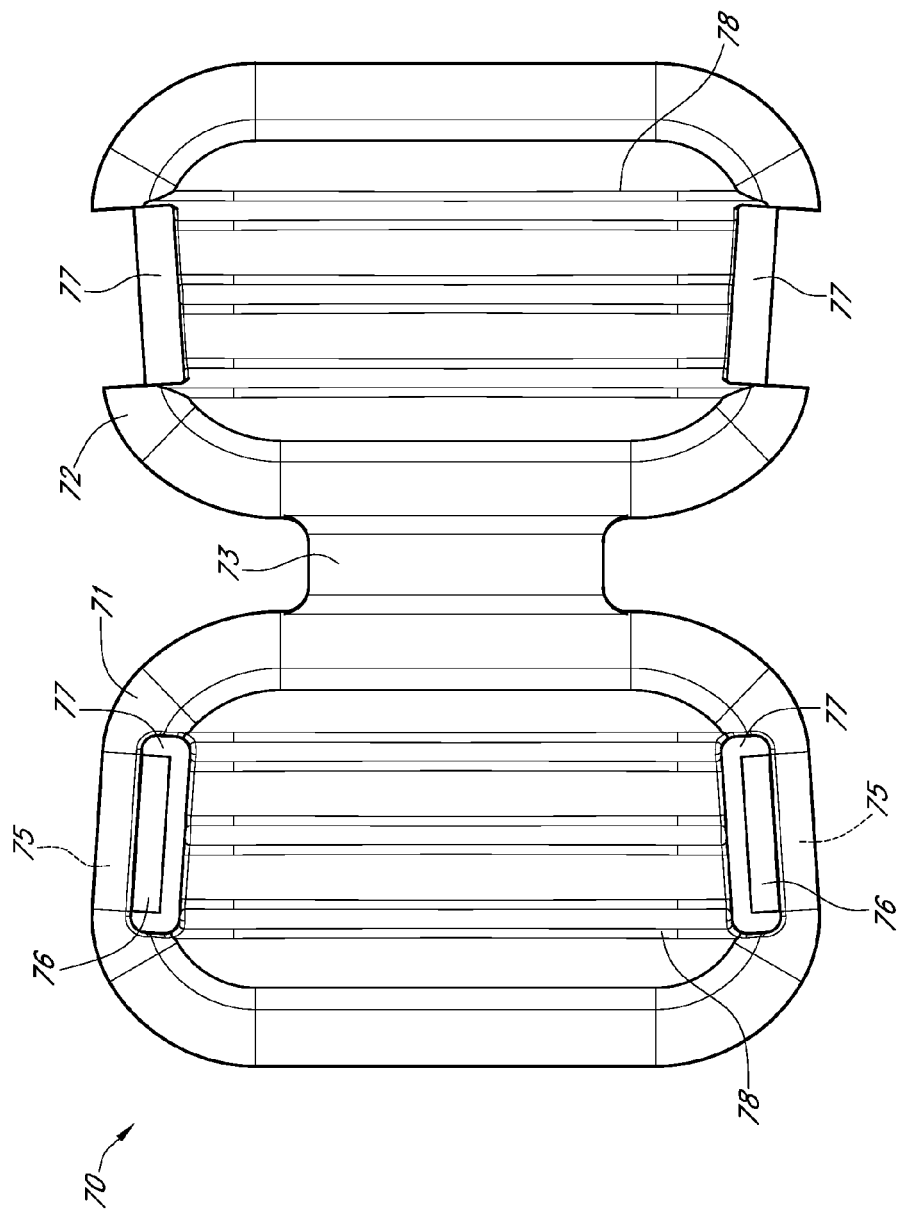

FIGS. 14 and 15 illustrate perspective and top views of an embodiment of a clasp 70. As described herein for band 50, clasp 70 is optional, and closure latch 10 can be provided with or without clasp 70. Clasp 70 can comprise any of many different structures that can attach, e.g., clasp or clamp, a portion of a band 50 to allow a user to more easily grasp and pull band 50. In some embodiments, clasp 70 comprises a first clasp member 71 and a second clasp member 72 configured to clasp around a distal portion of a band, as shown in FIGS. 2, 10A, 10B and 12. FIG. 14 shows interior surfaces of clasp members, and FIG. 15 shows their exterior surfaces. Clasp members 71 and 72 can comprise many shapes, such as substantially ovular, rectangular, circular, and the like, and can comprise the same or different shapes. Clasp members 71 and 72 can comprise any of the materials described herein for the first and second latch members of closure latch 10. In the exemplary embodiment, clasp members 71 and 72 comprise an approximately rectangular shape with rounded edges, and comprise a metal or plastic with sufficient rigidity to secure a portion of band 50 between members 71 and 72.

Members 71 and 72 can be connected by a connecting member 73 between members 71 and 72. Members 71 and 72, and connecting member 73 can be separately or integrally formed. In use, member 72 can be moved to rotate in direction 74 toward member 71 about connecting member 73, to clasp a portion of a band 50 (preferably the distal end of the fifth portion 50e of band 50, shown in phantom in FIG. 14) between members 71 and 72. Members 71 and 72 are in a closed or clasped position when clasping a portion of a band 50 therebetween. Members 71 and 72 can be held in a closed or clasped position in many different ways, such as mechanical fasteners, frictional fit, and the like. In the illustrated embodiment, member 71 or 72 can include a pair of tabs 75 each with a protruding lip 76, configured to be received by or held by a corresponding recess or shoulder 77 positioned on the other of member 71 or 72, when clasp 70 is in a closed position. A recess 77 can be configured to extend through member 71 or 72 proximate to tabs 75, through which a user can insert a tool to assist in the removal of tabs 75 and lips 76 from recess or shoulder 77, to move clasp 70 to an open position, and remove clasp 70 from band 50. In some embodiments, tabs 75 and lips 76 can be removed from recess or shoulder 77 by hand, to remove clasp 70 from band 50 without a tool.

Members 71 and 72 can comprise handling portions on their outer surfaces, similar to the other handling portions described herein, to assist a user in grasping clasp 70. In the exemplary embodiment, members 71 and 72 can include a handling portion comprising ribs 78. Members 71 and 72 can comprise opposed clamping surfaces 79, which can comprise similar structure and can function similarly to the other clamping surfaces described herein. In the exemplary embodiment, one or each clamping surface 79 can comprise a recessed groove 79a configured to receive an interlocking rib 79b positioned on the other clamping surface 79, and/or a recess 79c, of any shape (triangular in the illustrated embodiment), configured to receive an interlocking protrusion 79d positioned on the other clamping surface 79.

Figure 16A:
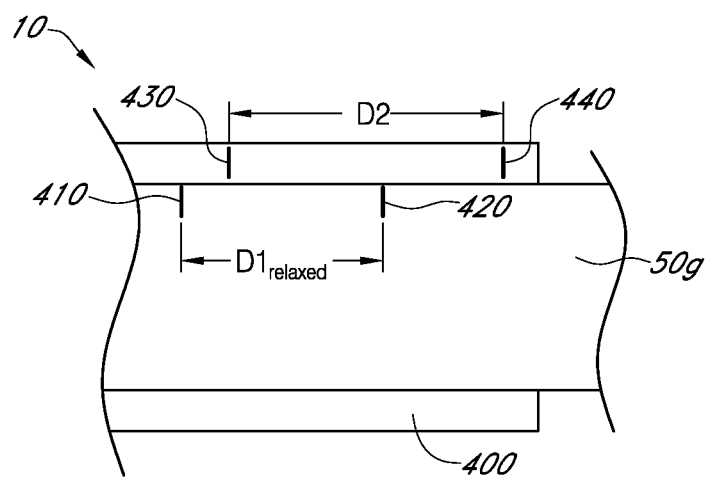
FIGS. 16A and 16B illustrate top views of a tension reading device proximate to a portion of a band, in relaxed and stretched states, respectively.
Figure 16B:
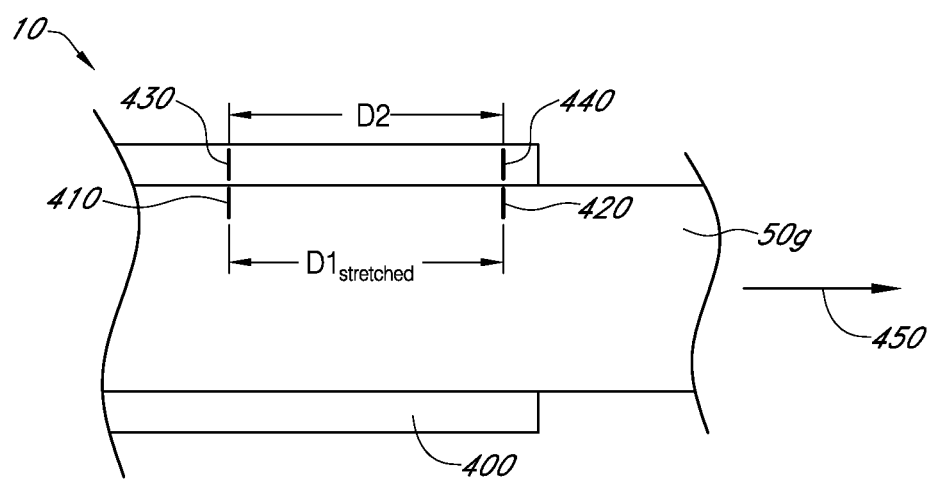

FIGS. 16A and 16B illustrate top views of a tension reading device 400 proximate to a portion 50g of band 50. Tension reading device 400 can be used to pull a band to a predetermined target tension by measuring the amount of stretch in an elastic portion of the band. Tension reading device 400 can be integrated into a portion of a clamping device, such as closure latch 10, as described further below. Tension reading device 400 can comprise a card, or other marked communication device that can be held proximate to a portion 50g of band 50.

FIG. 16A shows an elastic band portion 50g in a relaxed, or quiescent, state, and FIG. 16B shows portion 50g in a stretched state when band portion 50g is stretched in the direction shown by direction arrow 450. Referring to FIGS. 16A and 16B, portion 50g can comprise any portion of the band 50, including any of portions 50a-50f described herein. Preferably, portion 50g comprises an elastic or stretchable material, although the remainder of band 50 can comprise either an elastic or non-elastic material. Portion 50g can be marked with a first band tension marker 410 and a second band tension marker 420, spaced apart along a length of portion 50g. First band tension marker 410 and second band tension marker 420 can be separated by a distance that can vary as the portion 50g of the band is stretched or relaxed. The distance of separation between first band tension marker 410 and second band tension marker 420 is shown as $D1_{relaxed}$ in FIG. 16A, and $D1_{stretched}$ in FIG. 16B, to demonstrate how D1 can vary as portion 50g is relaxed and stretched. Thus, $D1_{stretched}$ in FIG. 16B can be greater than $D1_{relaxed}$ in FIG. 16A.

Tension reading device 400 can be marked with a first strap tension indicator 430 and a second strap tension indicator 440 spaced apart by a distance shown as tension indicator distance D2. Tension indicator distance D2 does not vary when portion 50g is relaxed and stretched.

As the band portion 50g is stretched, the user can compare the position of markings 410 and 420, and the distance of separation $D1_{stretched}$ to the position of indicators 430 and 440 and the target tension indicator distance D2 to facilitate stretching the band portion 50g to a predetermined target tension. The predetermined target tension can correspond to a condition in which the distance $D1_{stretched}$ is equal to a fraction or multiple of the tension indicator distance D2, such as ½, ⅓, ¼, ⅕, 2×, 3×, 4× or 5× the distance. Without limitation, in the exemplary embodiment of FIGS. 16A and 16B, the predetermined target tension in band portion 50g can correspond to a point wherein the portion 50g is stretched such that the distance of separation $D1_{stretched}$ is approximately equal to the tension indicator distance D2.

The user can compare the distance of separation $D1_{stretched}$ to the target tension indicator distance D2 to facilitate stretching the band portion 50g to a predetermined target tension, even if markers 410, 420, are not substantially aligned with indicators 430, 440, respectively, when band portion 50g is stretched to a predetermined target tension. In the exemplary embodiment of FIGS. 16A and 16B, when band portion 50g is stretched to a predetermined target tension, markings 410, 420, are substantially aligned with indicators 430, 440, respectively.

It will be understood that additional tension markers and indicators can be used, separated by varying distances that may differ from $D1_{stretched}$, $D1_{relaxed}$ and $D2$, to facilitate stretching the band portion 50g to various predetermined target tensions. Additionally, tension markers and indicators can be positioned on either or both sides of band portion 50g.

The above structure and methods for stretching a band to a predetermined tension can be used in any and many clamping devices. It will be understood that these structures and methods can be used in combination with the structures and methods described above for closure latch 10. For example, the user can open latch 10, stretch the portion 50g of band 50 to a predetermined target tension, and close latch 10, to clamp band 50 around an object 60 at a predetermined tension.

Figure 17:
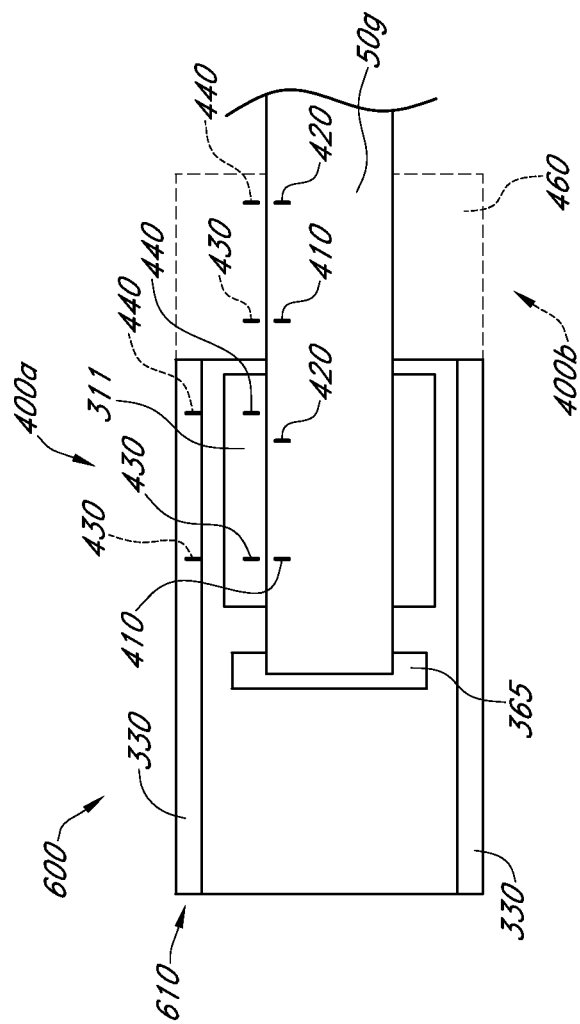
FIGS. 17-18 show embodiments of a tension reading device integrated into a closure latch device.
Figure 18:
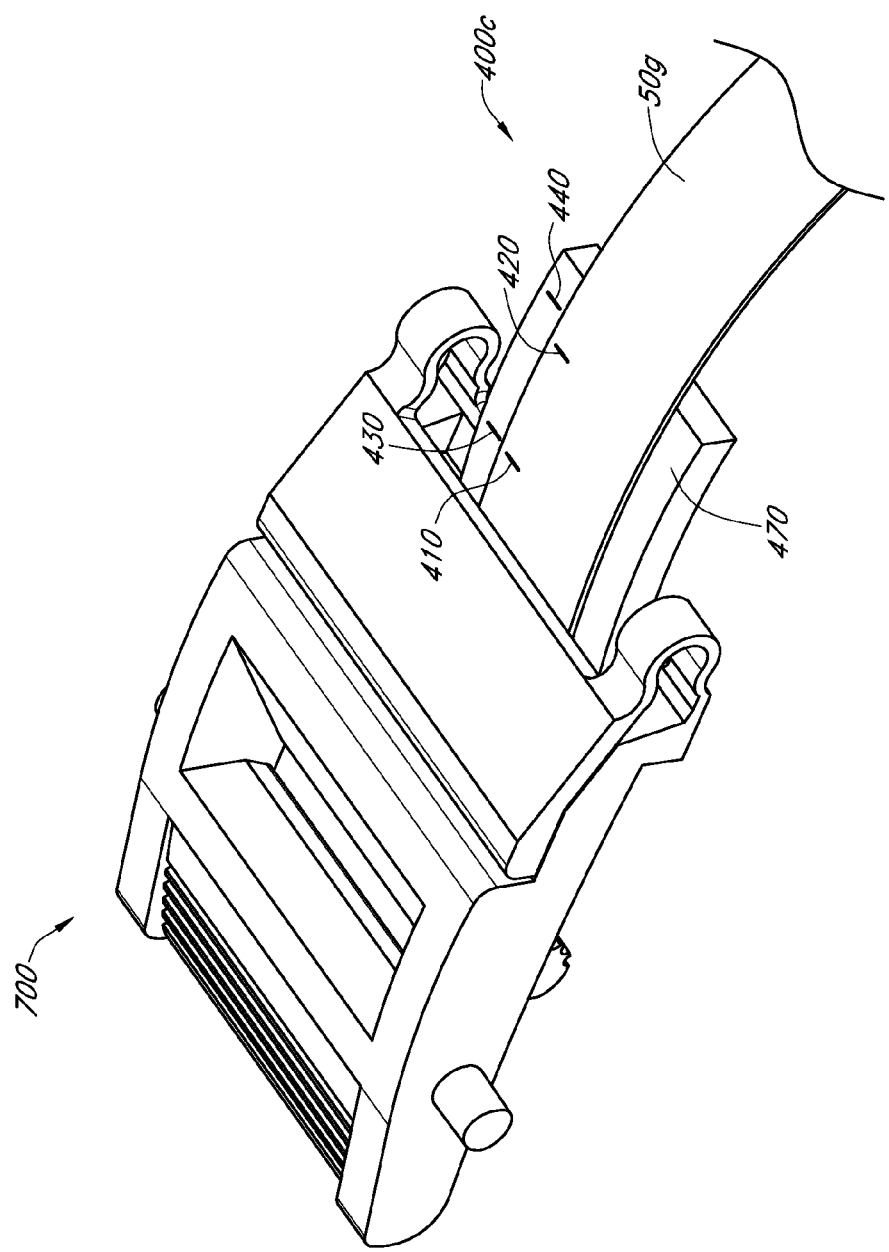

FIGS. 17-18 show various embodiments of a tension reading device integrated into a closure latch device, such as closure latch device 10 described herein.

FIG. 17 is a top view of a second latch member 610 with substantially similar features that function substantially similarly to the other second latch members described herein. One difference between second latch member 610 and the other second latch members described herein is that second latch member 610 includes a tension reading device 400a with tension indicators 430 and 440 spaced apart and positioned on surface 311. Alternatively or additionally, device 400a can comprise tension indicators 430 and 440 spaced apart and positioned on sidewall 330. In an alternative or additional embodiment, second latch member 610 can include a tension reading device 400b comprising a portion 460 that extends distally from a main body of second latch member 610, with indicators 430 and 440 positioned on portion 460. Using any or all of the embodiments in FIG. 17, tension reading devices 400a and/or 400b can be integrated into latch member 610 to assist a user in stretching a portion 50g of band 50 to a predetermined target tension, and thus function similarly to device 400 as described herein and shown in FIGS. 16A and 16B.

FIG. 18 shows a rear perspective view of an embodiment of a tension reading device 400c of a first latch member 700 with substantially similar features that function substantially similar to the other first latch members described herein. One difference between first latch member 700 and the other latch members described herein, is that first latch member 700 has a portion 470 that extends distally from a main body of first latch member 700. First latch member 700 can comprise tension indicators 430 and 440 spaced apart and positioned on portion 470. Tension reading device 400c can be integrated into latch member 700 to assist a user in stretching a portion 50g of band 50 to a predetermined target tension, and thus function similarly to device 400 as described herein and shown in FIGS. 16A and 16B.

The tension markers and tension indicators described herein can comprise ink, pigments, dyes, recessed or protruding "tick" marks, notches, slots, or other markers or indicators known in the art. In some embodiments, the second latch member 610 and/or the first latch member 700 can includes an opening, window, or substantially transparent portion, so that a user can more easily view the markers 410 and 420, and indicators 430 and 440.

FIGS. 19-20 and 22-23 show an embodiment of a closure latch 10A, comprising a first latch member 20A and second latch member 30A. FIG. 21 shows a front cross-sectional view of second latch member 30A taken along line 21-21 of FIG. 20 Many of the components of closure latch 10A, first latch member 20A, and/or second latch member 30A are substantially similar to the components of the other embodiments of closure latches, first latch members, and/or second latch members described above, except as otherwise noted herein.

Figure 19:
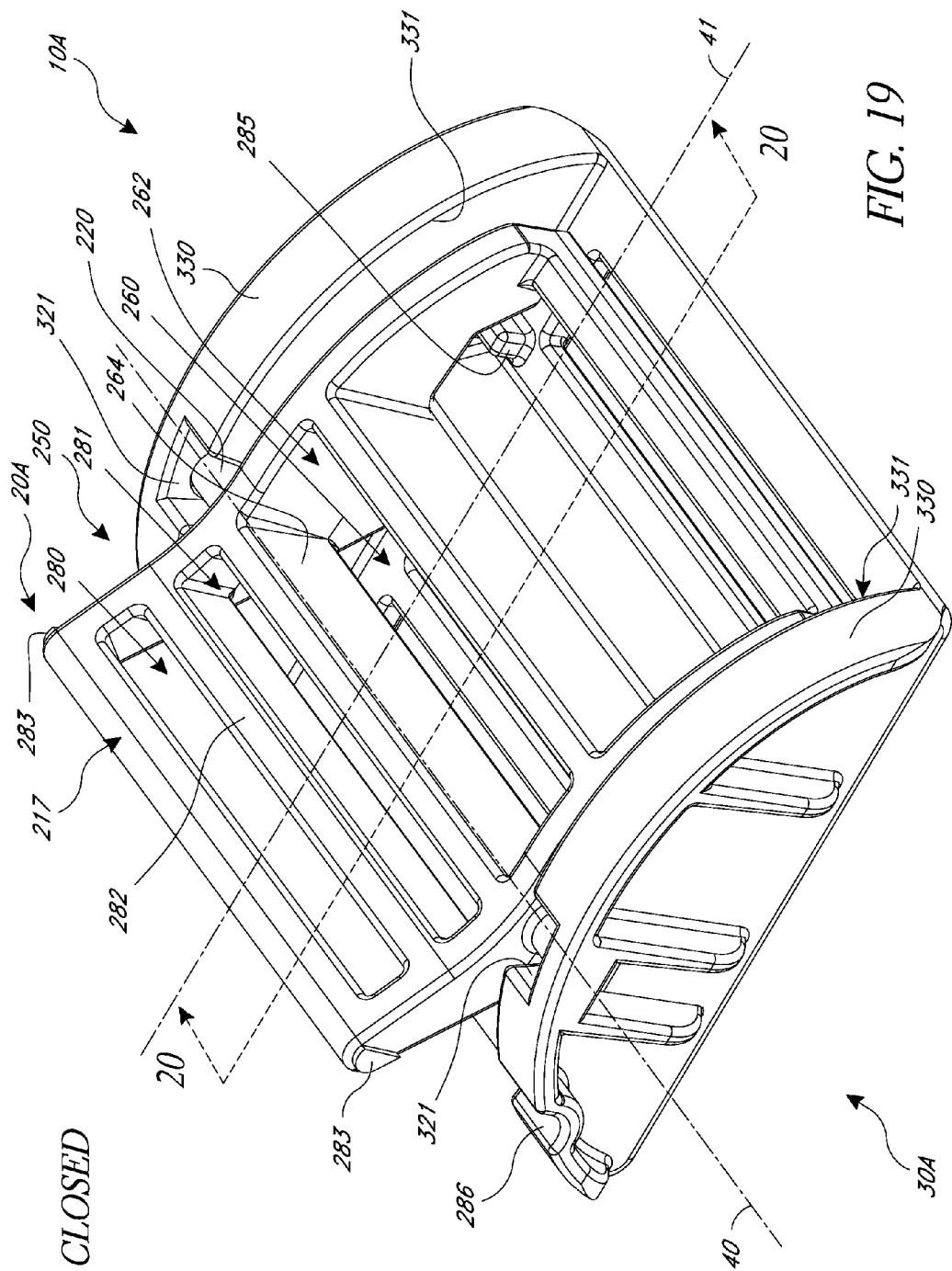
FIG. 19 shows a front and left side perspective view of an embodiment of a closure latch.
Figure 20:
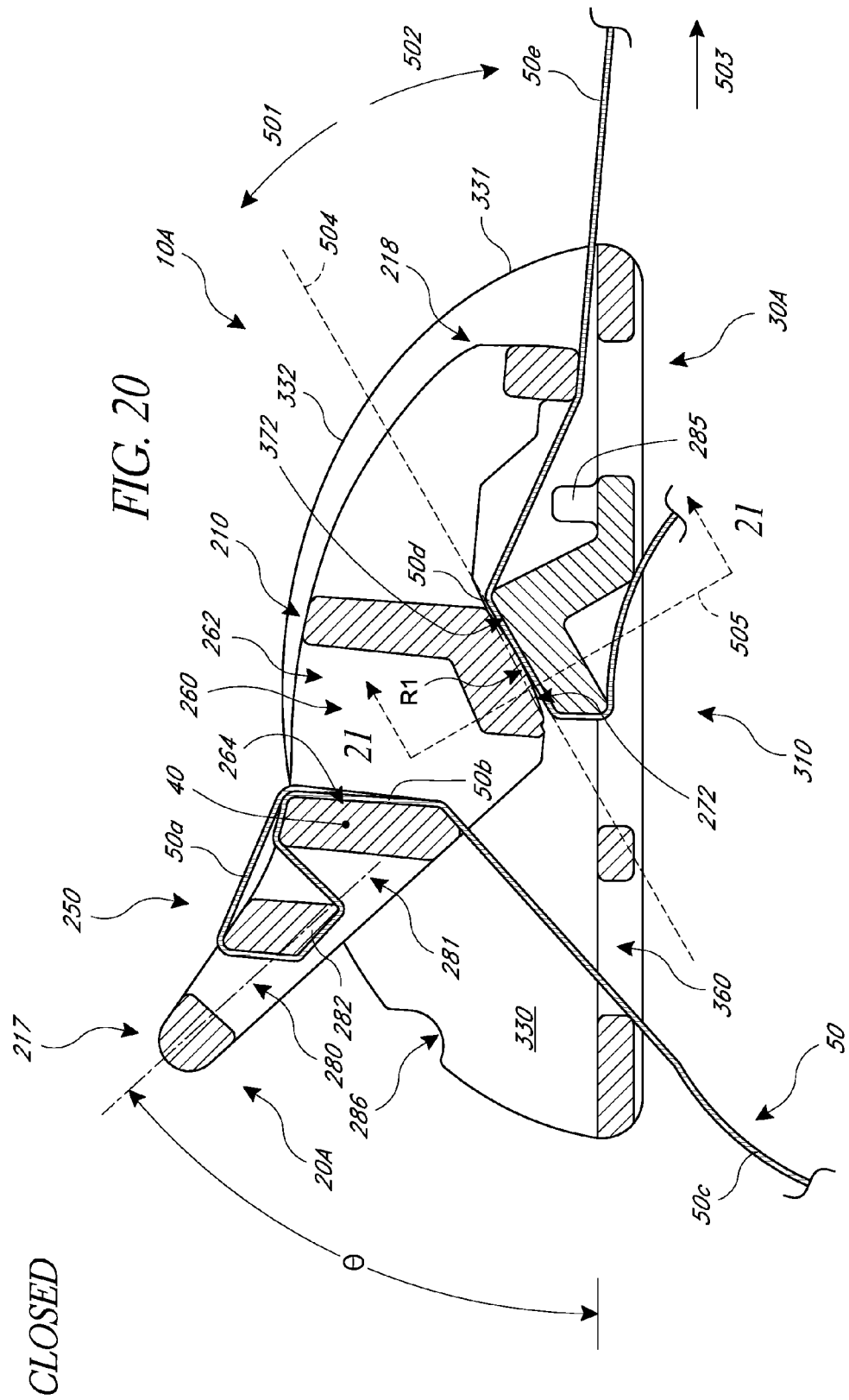
FIG. 20 shows a side cross-sectional view of an embodiment of a closure latch taken along line 20-20 of FIG. 19.
Figure 21:
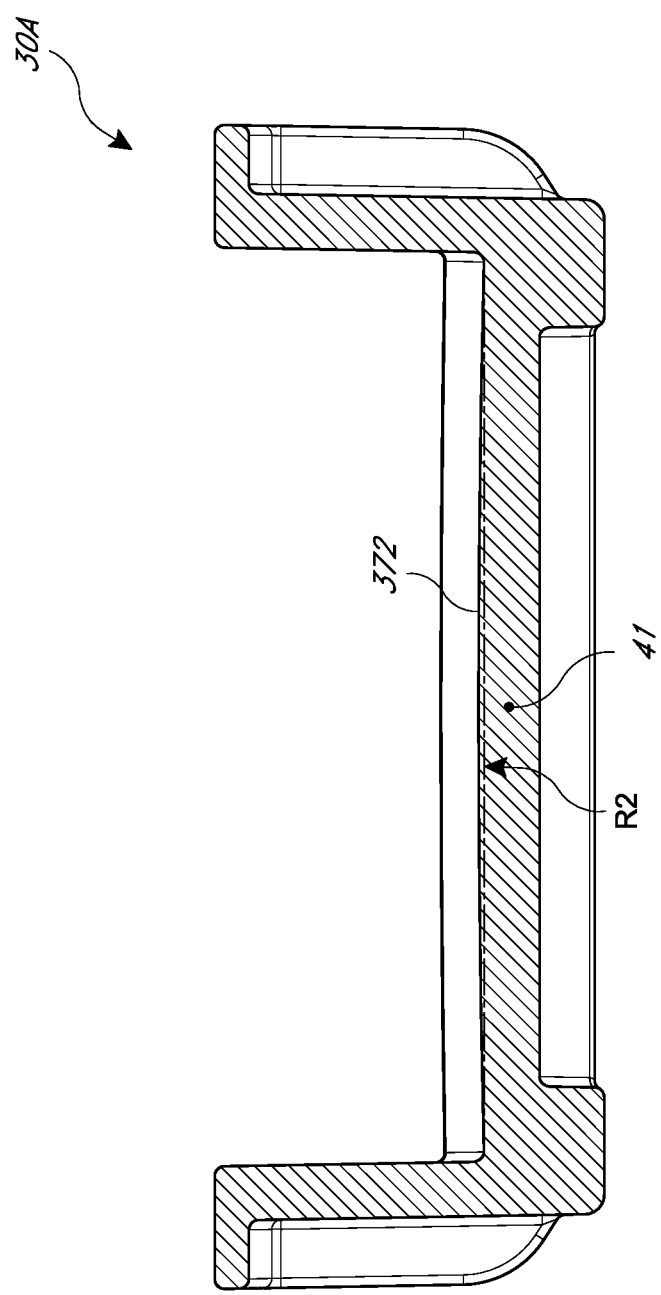
FIG. 21 shows a front cross-sectional view of an embodiment of a second latch member taken along line 21-21 of FIG. 20.

Referring to FIGS. 19 and 20, one difference is that the band attachment portion 250 on first latch member 20A can be positioned proximally with respect to opening 262 (e.g., on proximal portion 217). A portion of the band can extend through channel 260 towards opening 360 (FIG. 20), and guided by and along surface 264, which can be positioned distally with respect to band attachment portion 250, and proximally with respect to channel 260. In some embodiments, a portion of the band can maintain at least partial contact with surface 264 when the latch members 20A, 20B are in an open (FIG. 22) and closed position (FIGS. 19-20), to help guide a portion of the band (e.g., portion 50b) towards opening 360 (FIG. 20).

Alternatively or additionally, band attachment portion 250 can be configured with openings 280 and 281 extending through a portion of first latch member 20A to form a support portion 282 positioned therebetween. A portion of band 50 (e.g., a portion of first portion 50a) can extend through openings 280, 281 and be secured to another portion of band 50 to form a loop in band 50 around support 282. The loop can be formed in band 50 with any of the attachment ways described herein or known in the art, such as clamps, adhesives, thermal, chemical, or ultrasonic bonding, mechanical fasteners, and the like.

In some embodiments, proximal portion 217 can be configured to extend outwardly by a sufficient length and/or at a sufficient angle (e.g., upwardly) with respect to another portion of closure latch 10A (e.g., body 210 of first latch member 20A), to facilitate the movement or pivoting of first latch member 20A and second latch member 30A with respect to each other. In some embodiments, proximal portion 217 can extend from between the sidewalls 330 of second latch member 30A and beyond edges 331 of the sidewalls 330, and/or beyond the curvilinear plane 332 extending laterally between the edges 331 (FIG. 20). Proximal portion 217 can be configured to extend outwardly from second latch member 30A to facilitate handling of first latch member 20A and/or to allow a resistance element 283 (described below) to be positioned on proximal portion 217 without causing interference between latch members 20A, 30A when closure latch 10A is in a closed position, as described further below.

In the illustrated embodiment, proximal portion 217 can extend from body 210 at an angle θ, that is measured with respect to base 310 of second latch member 30A when latch 10A is in a closed, or clamped position. Angle θ can range from approximately 5 to 90 degrees, or more narrowly, from approximately 15 to 75 degrees, or even more narrowly, from approximately 35 to 65 degrees.

In some embodiments, closure latch 10A can comprise one or more latch resistance elements configured to reduce the likelihood of, or resist motion of latch members 20A, 30A with respect to each other. The resistance element(s) can comprise a separate piece, or can be attached to or integrally formed with latch member 20A and/or 30A. In a preferred embodiment, a resistance element can be implemented to hold latch member 20A in an open or unclamped position with respect to latch member 30A. Holding latch member 20A open can facilitate the use of latch 10A to secure a band around an object.

The resistance elements described herein can comprise any of a variety of structures that resist motion between latch members 20A and 30A. In some embodiments, the resistance elements are configured to allow latch members 20A and 30A to "lock" or resist motion by causing an engagement or holding interference between latch members 20A and 30A. The amount of force with which one or more resistance elements engage and hold latch members 20A and 30A in an open position is referred to as a "breakaway force." Once latch members 20A and 30A are engaged with one or more resistance elements, latch members 20A and 30A will remain engaged and in an open position until a closing force that is greater than or equal to the breakaway force is applied to latch members 20A and 30A. The closing force can be applied directly to the latch members 20A and 30A (e.g., when a user directly grasps and moves latches 20A, 30A), or can be applied to the latch members 20A, 30A by extending a band through closure latch 10A and applying tension to or tightening the band. Thus, after the resistance elements are engaged with latch members 20A and 30A, latch members 20A and 30A can disengage when a force is applied to latch members 20A and 30A that is greater than or equal to the breakaway force, and can resist motion when a force is applied to latch members 20A and 30A that is less than the breakaway force. Preferably, such engagement and disengagement between latch members 20A and 30A using the resistance elements described herein is repeatable.

Figure 22:
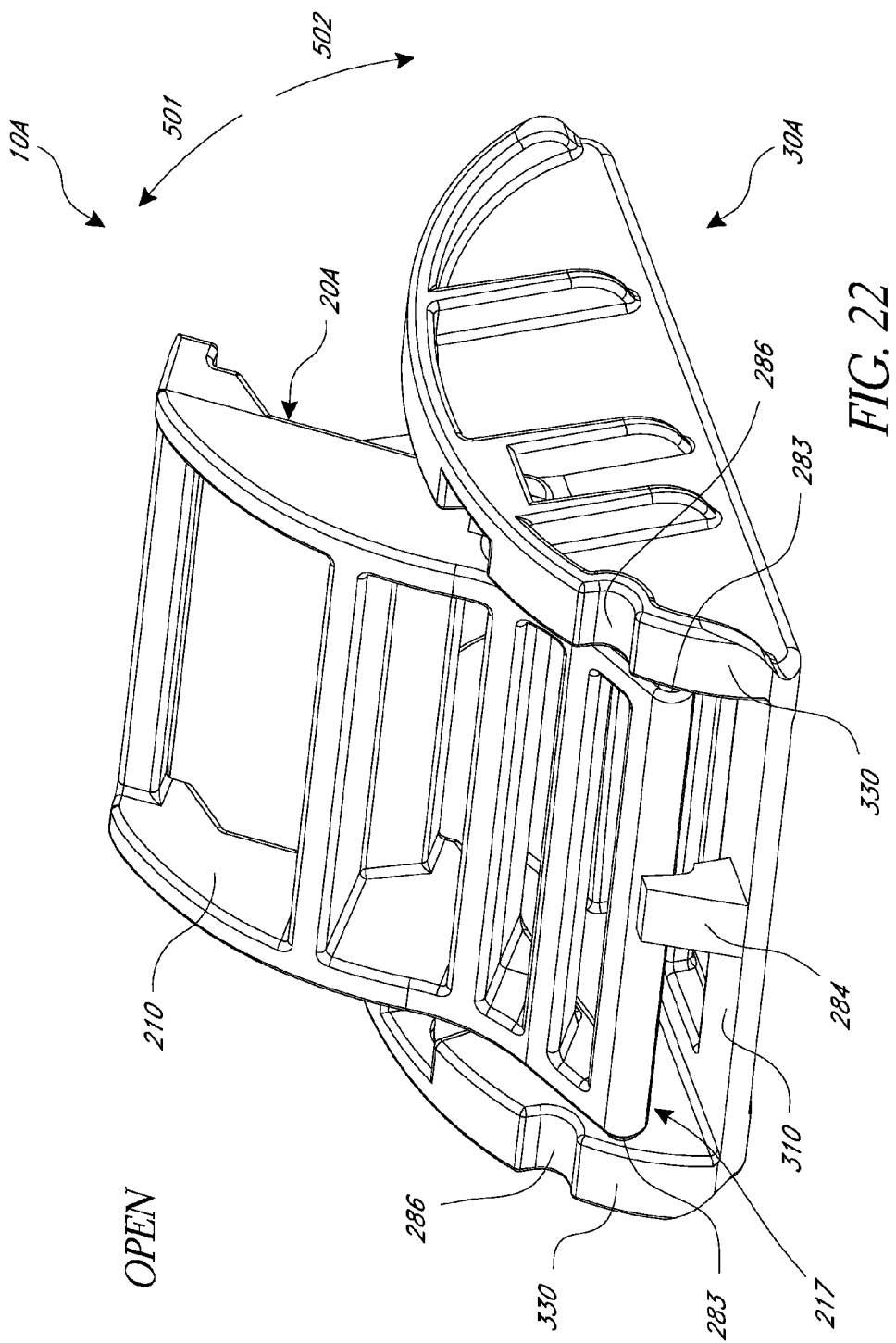
FIG. 22 shows a front and right side perspective view of an embodiment of a closure latch.

FIGS. 19 and 22 illustrate embodiments of a resistance element 283 (FIG. 19) and a resistance element 284 (FIG. 22) that can be implemented, separately, or in combination with each other and with the various embodiments of the closure latches described herein. The positioning and number of resistance elements 283, 284 on latch members 20A and 30A shown in FIGS. 19 and 22 are for illustrative purposes only. As such, resistance elements 283 and 284 can be positioned anywhere on latch members 20A and/or 30A that will facilitate engagement between latch members 20A and 30A when members 20A, 30A are moved to an open position with respect to each other. Any number of resistance elements 238 and/or 284 can be implemented with the closure latches described herein.

Referring to FIG. 19, resistance element 283 can comprise one or more tabs, nibs, bulbs, ribs, shoulders, flanges, protrusions, or any other structure on latch member 20A that will engage with and resist motion of latch member 20A with respect to latch member 30A when latch member 20A is in an open position (FIG. 22). In the illustrated embodiment, resistance element 283 extends (e.g., laterally) from a portion of latch member 20A (e.g., distal portion 217, or body 210) to allow interference with a portion of latch member 30A (e.g., sidewalls 330, or the inner surfaces of sidewalls 330). It will be understood that resistance element 283 can comprise a similar structure mounted on latch member 30A, such as an inner surface of sidewall 330, that engages (e.g. interferes) with a corresponding portion of latch member 20A. It will also be understood that although resistance element 283 engages or locks latch members 20A and 30A to each other with an interference fit, the resistance elements described herein can comprise other alternative locking or latching structure that will hold latch members 20A and 30A with a breakaway force and release latch members 20A and 30A when a force is applied to latch members 20A and 30A that is greater than or equal to the breakaway force.

Referring to FIG. 22, resistance element 284 can comprise one or more tabs, nibs, bulbs, ribs, shoulders, flanges, protrusions, or any other structure on latch member 30A that will engage with and resist motion of latch member 20A with respect to latch member 30A when latch member 20A is in an open position. In the illustrated embodiment, resistance element 284 extends (e.g., upwardly) from a portion of latch member 30A (e.g., a portion of base 310) to allow interference with a portion of latch member 20A (e.g., a portion of distal portion 217 or body 210). It will be understood that resistance element 284 can comprise a similar structure mounted on latch member 20A, such as a portion of distal portion 217 that interferes with a corresponding portion of latch member 30A, such as base 310.

Reference is now made to FIG. 20. In a method of use of latch 10A, a band 50 can be attached to band attachment portion 250, and routed through closure latch 10A, and using one or more steps that are similar to those described herein for routing band 50 through closure latch 10 (see, e.g., FIGS. 10A and 10B). In some embodiments, the band portion 50a can be extended through openings 280, 281 and secured to another portion of band 50 to form a loop in band 50 around support 282.

Next, latch member 20A can be moved to an open, or unclamped, position relative to second latch member 30A, by applying a force to distal portion 217, and moving latch member 20A in the direction shown by arrow 501. Latch member 20A can be moved with a sufficient force with respect to latch member 30A such that resistance element(s) 283 and/or 284 engage or lock latch members 20A and 30A with respect to each other, and held together at a breakaway force.

Next, band 50 can be pulled with a pulling force (e.g. by moving the band portion 50e) in the direction shown by arrow 503 (FIG. 20), causing a closing force that has a tendency to pull the first latch member 20A (e.g., clamping surface 272) and second latch member 30A (e.g., clamping surface 372) towards each other about pivot axis 40. When the pulling force and/or the closing force are less than or equal to the breakaway force between first latch member 20A and second latch member 30A caused by resistance element 283 and/or 284, the breakaway force will resist movement between members 20A, 30A.

When the pulling force and/or the closing force applied to latch members 20A, 30A are greater than or equal to the breakaway force caused by resistance element 283 and/or 284, the pulling force and/or closing force will overcome the breakaway force. Once the breakaway force is exceeded, members 20A, 30A can pivot toward each other with respect to pivot axis 40, and the closing force will cause the latch 10A to close. In the illustrated embodiment, the closing motion involves the first latch member 20A pivoting in direction 502 toward the second latch member 30A. In some embodiments, the breakaway force is a discrete point that is sufficiently high enough, that upon it being exceeded, latch 10A will "snap" or rapidly close. In some embodiments, a stop can be provided on a portion of first latch member 20A and/or second latch member 30A, to prevent overextension and/or damage of closure latch 10A during the rapid closure thereof. An exemplary stop 285 is shown in FIGS. 19 and 20.

In some embodiments, the configuration of resistance element 283 and/or 284 can be selected (e.g., by varying the interference between members 20A, 30A), to control the amount of pulling force on band 50 required to overcome the breakaway force between members 20A, 30A. Such embodiments allow closure latch 10A to be applied at a selected tension, which can provide for a patient's comfort and safety, while providing convenience of use to the user. For example, such embodiments can prevent overtightening of the band, which could cause loss of blood flow or other patient injury, and/or can prevent undertightening of the band, which can cause the object being secured by the band to break free, defeating the use for which the band is being applied. Preferably, the resistance element 283 and/or 284 produces a breakaway force approximately equal to a preferred band tension of the latch 10A.

Referring to FIGS. 20 and 21, latch members 20A and/or 30A can include clamping surfaces 272, 372, respectively, as described elsewhere herein with respect to other embodiments of closure latches (e.g., FIGS. 4, 7). The cross-sectional profile of clamping surface 272 and/or 372 can include substantially straight portions, and/or can be curved or radiused to improve the clamping of a portion of a band (e.g., band portion 50d, FIG. 20) positioned between surfaces 272 and 372. In some embodiments, the cross-sectional profile of clamping surface 272 and/or 372 can be substantially straight with respect to a first direction, and/or can be substantially curved or radiused with respect to a second direction. For example, clamping surface 272 and/or 372 can form a semi-cylindrical shape. In some embodiments, clamping surface 272 and/or 372 can comprise a curved or radiused cross-sectional profile that extends in two or more directions, to form, for example, a semi-spherical shape.

FIG. 20 shows an embodiment in which clamping surface 272 of first latch member 20A has a vertical-longitudinal cross-sectional profile (e.g., a cross-section taken along a plane that is parallel to longitudinal axis 41 of FIG. 19 and generally perpendicular to base 310 of second latch member 30A) that is curvilinear and convex with respect to clamping surface 372 of second latch member 30A. In some embodiments, such a vertical-longitudinal cross-sectional profile is substantially circular with a radius R1. In some embodiments, the illustrated clamping surface 272 has a vertical-longitudinal cross-sectional profile that is substantially uniform throughout a width (i.e., the dimension aligned with pivot axis 40) of the clamping surface 272, such that a horizontal-longitudinal cross-sectional profile (e.g., a cross-section taken along a plane that is generally parallel to base 310) of the surface 272 is linear. In other embodiments, the horizontal-longitudinal cross-sectional profile of the clamping surface 272 is curved and preferably convex with respect to clamping surface 372 of second latch member 30A. When latch members 20A, 30A are in a closed position, and surfaces 272 and 372 clamp together against the portion 50d of a band, the forces between latch members 20A and 30A can at least partially flex or flatten the curved surface 272, providing additional clamping surface area of contact between clamping surfaces 272 and 372. In embodiments in which the vertical-longitudinal cross-sectional profile of clamping surface 272 is circular, R1 can range from approximately 0.1 to 3.0 inches, or more narrowly, from approximately 0.1 to 1.5 inches, or even more narrowly, from approximately 0.25 to 0.75 inches.

Reference is now made to FIGS. 20 and 21. Let a "tangent plane" 504 be defined as a plane that extends through a point of contact between the clamping surfaces 272 and 372 when the clamping surfaces contact each other (in the closed position of the latch 10A), wherein the tangent plane 504 is tangent to both of the clamping surfaces. Further, let a "normal plane" 505 be defined as a plane that is perpendicular to the tangent plane 504 and parallel to pivot axis 40. FIG. 21 shows an embodiment in which clamping surface 372 of second latch member 30A has a cross-sectional profile taken along the normal plane 505 that is curvilinear and convex with respect to clamping surface 272 of first latch member 20A. In some embodiments, such a cross-sectional profile is substantially circular with a radius R2. In some embodiments, such a cross-sectional profile of the illustrated clamping surface 372 is substantially uniform throughout a dimension that is parallel to both the tangent plane 504 and the longitudinal axis 41 of FIG. 19, such that a vertical-longitudinal cross-sectional profile (i.e., a vertical cross-section that is parallel to longitudinal axis 41) of the surface 372 is linear, as shown in FIG. 20. In other embodiments, the vertical-longitudinal cross-sectional profile of the clamping surface 372 is curved and preferably convex with respect to clamping surface 272 of first latch member 20A. When latch members 20A, 30A are in a closed position and surfaces 272 and 372 clamp together against the portion 50d of a band (FIG. 20), the forces between latch members 20A and 30A can at least partially flex or flatten the curved surface 372 (FIG. 21), providing additional clamping surface area of contact between clamping surfaces 272 and 372. In embodiments in which the clamping surface 372 has a circular cross-sectional profile taken along the normal plane 505, R2 can range from approximately 10 to 130 inches or more narrowly, from approximately 25 to 105 inches, or even more narrowly, from 45 to 85 inches.

Figure 23:
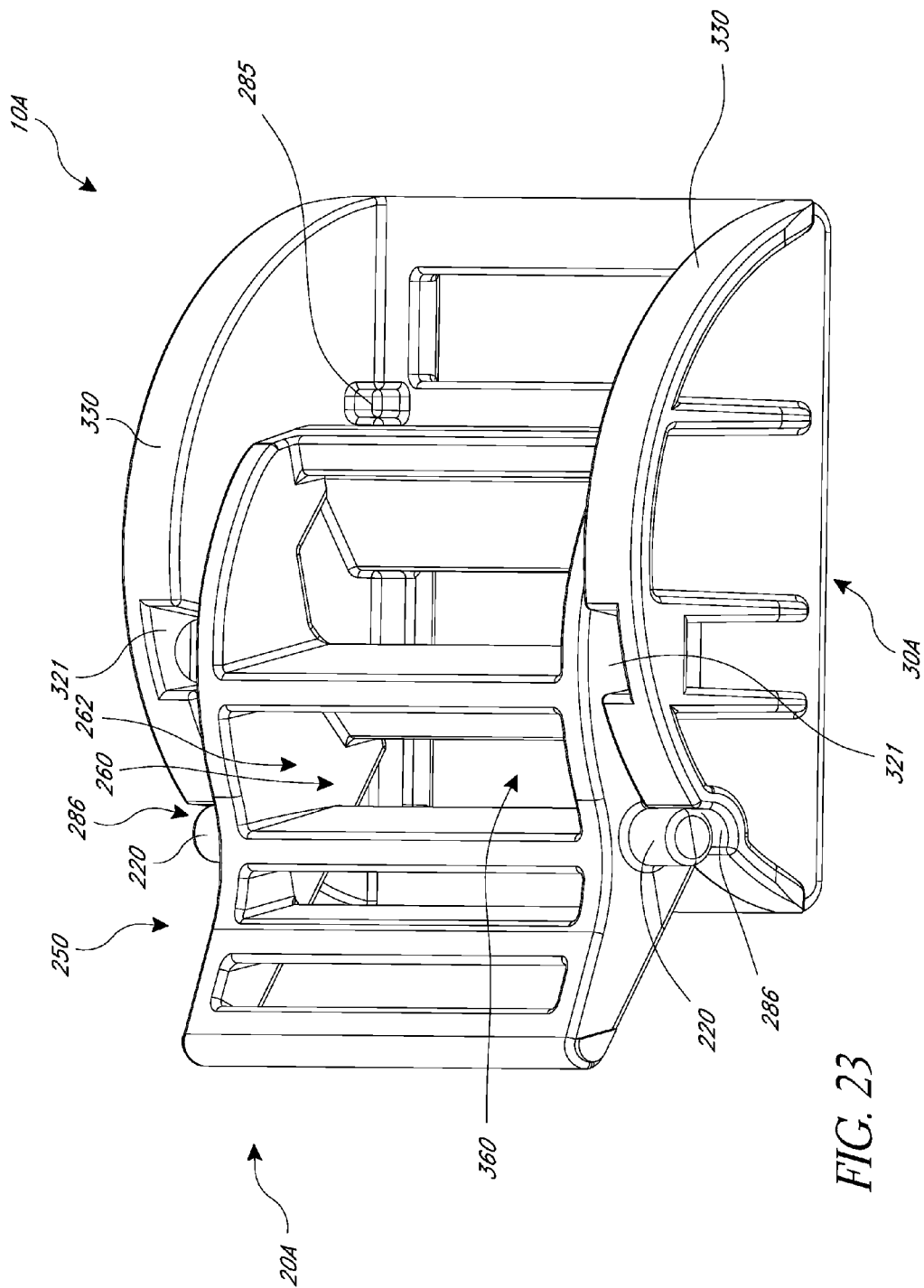
FIG. 23 shows a top and left side perspective view of an embodiment of a closure latch during assembly.

FIG. 23 shows a top and left side perspective view of an embodiment of a closure latch during assembly. Referring to FIGS. 19-20 and 22-23, second latch member 30A can include engagement portions or recesses 286 configured to support engagement portions of first latch member 20A during assembly. For example, referring to FIG. 23, a pair of recesses 286 can be configured to receive (e.g., removably receive) a pair of rotational members 220 at a position proximal to a pair of engagement portions 321 (e.g., grooves or recesses) that receive the members 220 during clamping usage of the closure latch 10A. Recesses 286 allow opening 262 on latch element 20A to be approximately vertically aligned with opening 360 on latch element 30A. Such alignment can facilitate the routing and insertion of band 50 through the openings 360 and 262, prior to attaching band 50 to attachment portion 250 of the first latch member 20A of the closure latch 10A. While the rotational members 220 of first latch member 20A are received within the recesses 286 of second latch member 30A, the members 220 preferably allow the first latch member 20A to pivot and rotate with respect to second latch member 30A, about the axis defined by the rotation members 220. This allows for more handling flexibility to help a user route the band through the latch members. After band 50 is attached and routed through closure latch 10A (FIG. 20), the rotational members 220 of latch element 20A can be removed from recesses 286 and engaged with grooves 321, as described further herein.

Although certain preferred embodiments and examples have been discussed herein, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the present disclosure, including the appended claims.

What is claimed is:

1. A closure latch comprising:
   a band comprising a first portion, a second portion, and a third portion;
   a first latch member comprising:
      a band attachment portion configured to secure the first portion of the band to the first latch member; and
      a first clamping surface; and
   a second latch member engaged with the first latch member such that the first and second latch members can pivot relative to each other about a pivot axis, the second latch member comprising a second clamping surface;
   wherein the first portion of the band is secured to the band attachment portion of the first latch member while the second portion of the band is positioned between the first and second clamping surfaces, such that tension in the band between the first and second band portions causes the first band portion to pull the first latch member, which in turn causes the first latch member to rotate about the pivot axis towards the second latch member, which in turn causes the first and second clamping surfaces to clamp onto the second band portion at a clamping point, wherein the third portion extends from the first portion of the band to the second portion of the band, and wherein the third portion of the band is positioned between the pivot axis and the clamping point.

2. The closure latch of claim 1, wherein the band is elastic.

3. The closure latch of claim 2, wherein the band includes a first band tension marker and a second band tension marker spaced apart along a portion of a length of the band, the first band tension marker and the second band tension marker separated by a tension marker distance that varies as the elastic band is stretched or relaxed; and
   a first band tension indicator and a second band tension indicator spaced apart by a tension indicator distance along a portion of the first latch member or the second latch member, wherein a user of the closure latch can stretch the elastic band to a predetermined target tension by adjusting the tension marker distance to be approximately equal to the tension indicator distance.

4. The closure latch of claim 3, wherein the first or second latch member includes a visual indication, in association with the first and second band tension indicators, of either the predetermined target tension or an application for which the predetermined target tension is recommended.

5. The closure latch of claim 3, wherein the first and second band tension indicators comprise a subset of a plurality of band tension indicators on the first latch member or the second latch member, wherein each unique adjacent pair of the band tension indicators are spaced apart at a distance that is different than the other unique adjacent pairs of the band tension indicators, each unique adjacent pair of the band tension indicators representing a different band tension produced by stretching the first and second band tension markers to be spaced apart by the distance between the two band tension indicators.

6. The closure latch of claim 5, wherein the band tension associated with each unique adjacent pair of the band tension indicators is indicated on the first latch member or on the second latch member in association with the unique adjacent pair of band tension indicators corresponding to the band tension.

7. The closure latch of claim 1, wherein the first clamping surface is positioned on a lower portion of the first latch member.

8. The closure latch of claim 1, wherein the second clamping surface is positioned on an upper portion of the second latch member.

9. The closure latch of claim 1, further comprising a loop in the band into which an object can be inserted, the loop extending from the first portion of the band to the second portion of the band.

10. The closure latch of claim 1, wherein the band attachment portion comprises a support around which the first portion of the band can be secured by forming a loop in the first portion of the band.

11. The closure latch of claim 1, further comprising:
    a latch resistance element;
    wherein the first latch member can rotate in a first direction with respect to the second latch member about the pivot axis to a closed position in which the first and second clamping surfaces clamp together;
    wherein the first latch member can rotate about the pivot axis in a second direction with respect to the second latch member to an open position wherein the first and second clamping surfaces do not clamp together; and
    wherein the latch resistance element is configured to hold the first latch member in the open position with respect to the second latch member, the latch resistance element configured to release the first latch member from the open position when a force tending to move the first latch member to the closed position is greater than or equal to a breakaway force associated with the latch resistance element.

12. The closure latch of claim 11, wherein the latch resistance element is positioned on at least one of the first latch member and the second latch member.

13. The closure latch of claim 12, wherein the latch resistance element comprises one or more protrusions extending from one of the first and second latch members, the one or more protrusions configured to engage with the other of the first and second latch members when the first latch member is in the open position with respect to the second latch member.

14. The closure latch of claim 13, wherein the protrusions frictionally engage with the other of the first and second latch members when the first latch member is in the open position with respect to the second latch member.

15. The closure latch of claim 11, wherein:
    the first latch member further comprises a band-routing opening extending through a portion of the first latch member; and
    the second latch member further comprises:
       a first pair of engagement portions releasably engaged with a corresponding pair of engagement portions of the first latch member in a manner that permits said rotation of the first latch member with respect to the second latch member, such that the pivot axis is defined by the engagement of the first pair of engagement portions with the corresponding pair of engagement portions of the first latch member;
       a second pair of engagement portions configured to releasably engage with the corresponding pair of engagement portions on the first latch member; and
       a band-routing opening extending through a portion of the second latch member;
    wherein the opening extending through the portion of the first latch member and the opening extending through the second latch member are substantially aligned with respect to each other when the pair of engagement portions of the first latch member are engaged with the second pair of engagement portions of the second latch member.

16. The closure latch of claim 15, wherein the second latch member comprises a base with a pair of sidewalls attached to the base, the first and second pairs of engagement portions positioned on the sidewalls.

17. The closure latch of claim 1, wherein at least one of the first and the second clamping surfaces is convex in at least one dimension with respect to the other of the first and second clamping surfaces.

18. The closure latch of claim 1, wherein the first latch member comprises a proximal portion that extends upwardly from the second latch member when the first latch member is in the closed position with respect to the second latch member.

19. The closure latch of claim 1, further comprising a stop positioned on at least one of the first and the second latch members, the stop configured to stop rotation of the first latch member with respect to the second latch member in the first direction when the first latch member is in the closed position.

* * * * *